United States Patent
Svensson et al.

(12) 
(10) Patent No.: US 6,656,469 B1
(45) Date of Patent: Dec. 2, 2003

(54) NICOTINE IMMUNOGEN

(75) Inventors: Torgny Svensson, Lidingo (SE); Anette Johansson, Jarlasa (SE)

(73) Assignee: Independent Pharmaceutica AB, Stockholm (SE)

( * ) Notice: Subject to any disclaimer, the term of this patent is extended or adjusted under 35 U.S.C. 154(b) by 0 days.

(21) Appl. No.: 09/700,718

(22) PCT Filed: May 28, 1999

(86) PCT No.: PCT/SE99/00920

§ 371 (c)(1),
(2), (4) Date: Dec. 28, 2000

(87) PCT Pub. No.: WO99/61054

PCT Pub. Date: Dec. 2, 1999

(30) Foreign Application Priority Data

May 29, 1998 (SE) ............................................. 9801923

(51) Int. Cl.[7] ............................................... A61K 39/00
(52) U.S. Cl. .............................. 424/184.1; 424/193.1; 514/343; 530/350; 530/401; 530/405; 546/279.4
(58) Field of Search ........................... 424/193.1, 184.1; 514/343; 530/350, 405, 409; 546/279.4

(56) References Cited

U.S. PATENT DOCUMENTS 5,723,477 A * 3/1998 McDonald et al.
5,876,727 A * 3/1999 Swain et al.

FOREIGN PATENT DOCUMENTS

WO WO 9203163 A 3/1992
WO WO 9630049 A 10/1996
WO WO 9814216 A 4/1998

OTHER PUBLICATIONS

Stedman's Medical Dictionary (24th edition; 1982; Waverly Press, Inc. Baltimore; pp. 695 and 88).*
Yoko Hieda et al., "Active Immunization Alters the Plasma Nicotine Concentration in Rats1", The Journal of Pharmacology and Experimental Therapeutics, 1997.
A. Castro et al., "Nicotine Enzyme Immunoassay", 1986, Research Communication in Chemical Pathology and Pharmacology.

* cited by examiner

Primary Examiner—Patrick J. Nolan
(74) Attorney, Agent, or Firm—Bacon & Thomas, PLLC

(57) ABSTRACT

A 5- or 6-nicotinyl-linker-carrier protein compound and immunogen having formula (a) wherein X is —NH—CO— or NH— or —C≡C— or —C=C— or $CH_2$—; Y is —$(CH_2)_k$— or —$(CH_2)_m$—$C_6H_{10}$—$(CH_2)_n$— or $(CH_2)_m$—$C_6H_4$—$(CH_2)_n$— when Z is —NH—, with the proviso that X is not —NH—CO— when Y is $(CH_2)_5$ and Z is —NH—, and X is —NH—CO— or —C≡C— or —C=C— or $CH_2$—, Y is —$(CH_2)_m$—$C_6H_{10}$—$(CH_2)_n$— or —$(CH_2)_m$—$C_6H_4$—$(CH_2)_n$—, when Z is —CO—, and X is —C≡C— or —C=C—, Z is —CO—, when Y is $(CH_2)_k$—, is disclosed. The compound may be used as a medicament, suitably in the form of a pharmaceutical composition. Additionally, a method of prophylactic and/or therapeutic immunological treatment of nicotine dependence from tobacco products to achieve harm reduction is described.

9 Claims, 9 Drawing Sheets

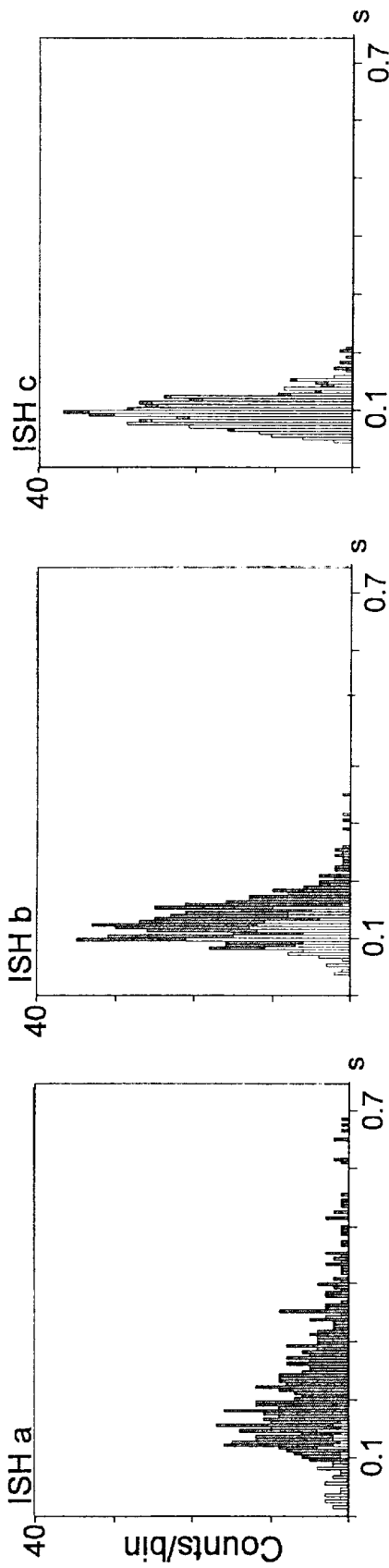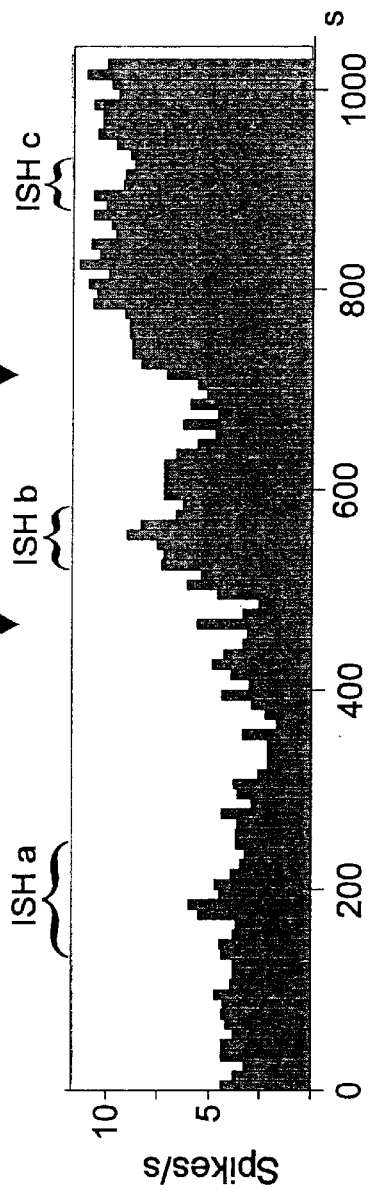
Fig. 5

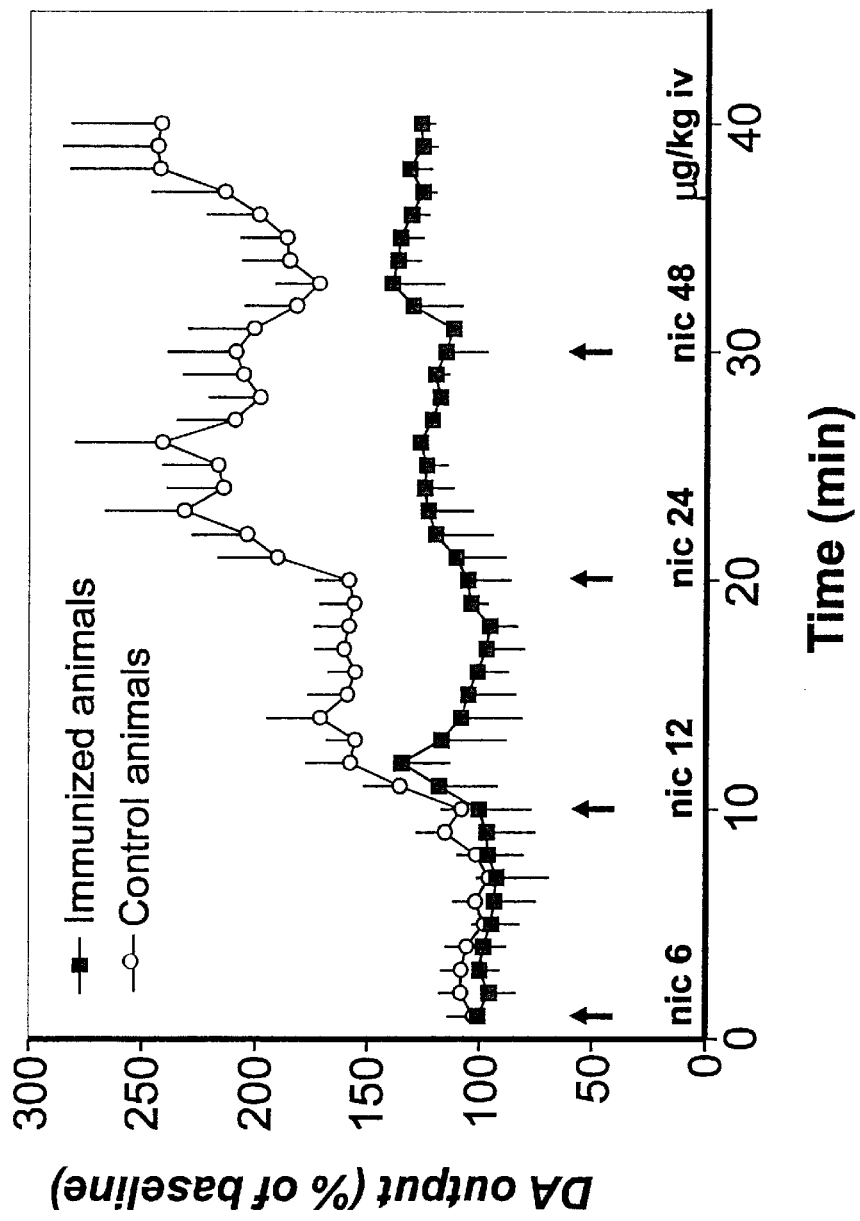

NICOTINE IMMUNOGEN

The present invention relates to a nicotine immunogen, to a 5- or 6-nicotinyl-linker-protein and its use as a medicament and a pharmaceutical composition comprising the 5- or 6-nicotinyl-linker-protein, and to a method of prophylactic and/or therapeutic immunological treatment of nicotine dependence from tobacco products to achieve harm reduction.

BACKGROUND OF THE INVENTION

Due to the vast number of tobacco users/smokers in the world who want to get rid of their dependence, there is a large market for products helping them to reach their goal or at least result in harm reduction.

One approach is to develop a vaccine/immunogen that in an individual can elicit antibodies which strongly bind to administered/inhaled nicotine and block its effect before it reaches their central nervous system. The idea is that if the individual does not experience the expected stimulating effect of nicotine administration/smoking, the interest in administering a tobacco product, such as moist snuff, or lighting a cigarette will cease (extinction/prevention).

A complementary approach is to develop an immunogen that in an individual can elicit antibodies which moderately or weakly bind to administered/inhaled nicotine and enhance/prolong its effect in their central nervous system. The idea is that if the individual experiences the expected stimulating effect of nicotine administration/smoking during a prolonged period of time, the interest in a renewed administration of a tobacco product, such as moist snuff, or lighting a cigarette will be postponed and the medical consequences of the tobacco product consumption will be reduced.

Both of the above mentioned approaches use immunogens which in an individual induces an immunological response which leads to harm reduction.

In the prior art there are papers describing immunoassays using antibodies directed to nicotine, but such antibodies have not been suggested for any medical use (See e.g. Castro A. and Monji N. Res. Comm. Chem. Path. Pharmacol. 1986,51, 393–404.)

The idea of treating nicotine dependence with a vaccine is not new, since it is comprised by earlier general disclosures of manufacturing vaccines against drugs which may cause a dependence (see e.g. EP-B1-0 496 839, exemplified by morphine; and WO 96/30049, exemplified by cocaine).

A paper disclosing active immunization to alter nicotine distribution was recently published (Hieda Y. et al, J. Pharmacol. and Exp. Therap. 1997,283, 1076–1081). The immunogen used in the experiments was (±)-6-(carboxymethyl-ureido)-nicotine linked to keyhole limpet hemocyanin.

Recently, the international patent application WO 98/14216 was published (Sep. 04, 1998). This application claims a large number of hapten-carrier conjugates based on the nicotine molecule and the common structural feature of the compounds seems to be that all of the hapten molecules contain a terminal carboxylic acid group which is then conjugated to the carrier. No in vivo testing has been disclosed for the alleged drug abuse treatment.

DESCRIPTION OF THE INVENTION

The present invention is directed to a nicotine immunogen comprising a 5- or 6-nicotinyl-linker-carrier protein having the formula

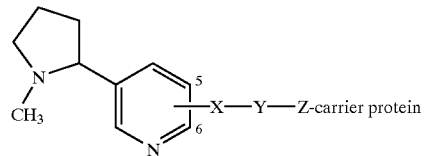

wherein
X is —NH—CO— or —NH— or —C≡C— or —CH=CH— or —CH$_2$—;
Y is —(CH$_2$)$_k$— or —(CH$_2$)$_m$—C$_6$H$_{10}$—(CH$_2$)$_n$— or —(CH$_2$)$_m$—C$_6$H$_4$—(CH$_2$)$_n$—
wherein k=0–20, m=0–6, and n=0–6, when
Z is —NH—,
with the provisio that X is not —NH—CO— when Y is (CH$_2$)$_5$ and Z is —NH—,
and
X is —NH—CO— or —C≡C— or —CH=CH— or —CH$_2$—,
Y is —(CH$_2$)$_m$—C$_6$H$_{10}$—(CH$_2$)$_n$— or —(CH$_2$)$_m$—C$_6$H$_4$—(CH$_2$)$_n$—
wherein m=0–6, and n=0–6, when
Z is —CO—,
and
X is —C≡C— or —CH=CH—,
Z is —CO—, when
Y is —(CH$_2$)$_k$—
wherein k=0–20.

In a preferred embodiment of the invention the 5- or 6-nicotinyl-linker-carrier proteins are selected from compounds wherein k=1–8, m=0–3 and n=0–3.

Other names for the 5- or 6-nicotinyl-linker-carrier protein are 5-(1-methyl-2-pyrrolidinyl)-2- or 3-pyridinyl-linker-carrier protein and 5-(N-methyl-2-pyrrolidinyl)-2- or 3-pyridinyl-linker-carrier protein.

The carrier protein of the 5- or 6-nicotinyl-linker-carrier protein of the invention may be selected from pharmaceutically acceptable proteins which coupled to a hapten are suitable for eliciting antibodies in humans, and is for example selected from the group consisting of keyhole limpet hemocyanin (KLH), tetanus toxoid, diphtheria toxoid, non-toxic mutant diphtheria toxoid CRM$_{197}$, outer membrane protein complex (OMPC) from Neisseria meningitidis, the B subunit of heat-labile *Escherichia coli*, and recombinant exoprotein A from *Pseudomonas aeruginosa* (rEPA).

The present invention is further directed to a 5- or 6-nicotinyl-linker-carrier protein having the formula

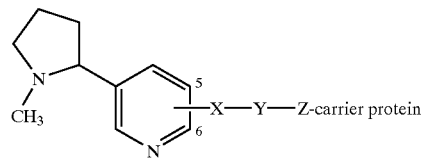

wherein
X is —NH—CO— or —NH— or —C≡C— or —CH=CH— or —CH$_2$—;
Y is —(CH$_2$)$_k$— or —(CH$_2$)$_m$—C$_6$H$_{10}$—(CH$_2$)$_n$— or —(CH$_2$)$_m$—C$_6$H$_4$—(CH$_2$)$_n$— wherein k=0–20, m=0–6, and n=0–6, when

Z is —NH—,
with the provisio that X is not —NH—CO— when Y is (CH$_2$)$_5$ and Z is —NH—, and X is —NH—CO— or —C≡C— or —CH=CH— or —CH$_2$—, Y is —(CH$_2$)$_m$—C$_6$H$_{10}$—(CH$_2$)$_n$— or —(CH$_2$)$_m$—C$_6$H$_4$—(CH$_2$)$_n$—
wherein m=0–6, and n=0–6, when Z is —CO—, and X is —C≡C— or —CH=CH—, Z is —CO—, when Y is —(CH$_2$)$_k$—
wherein k=0–20.

Also in this aspect of the invention the carrier protein may be selected from the group consisting of keyhole limpet hemocyanin (KLH), tetanus toxoid, diphtheria toxoid, non-toxic mutant diphtheria toxoid CRM$_{197}$, outer membrane protein complex (OMPC) from *Neisseria meningitidis*, the B subunit of heat-labile *Escherichia coli*, and recombinant exoprotein A from *Pseudomonas aeruginosa* (rEPA).

Further, the invention is directed to the new 5- or 6-nicotinyl-linker-carrier proteins according to the invention for use as a medicament, such as the immunizing component in a vaccine.

One compound excluded from the compounds of the above formula of the invention has been previously disclosed by Castro A. and Monji N. (ibid.), namely the 6-nicotinyl-linker-carrier protein wherein the carrier protein is bovine serum albumin and the linker is —NH—CO—(CH$_2$)$_5$—NH—. However, this compound has not been suggested for medical use.

The invention is additionally directed to a pharmaceutical composition comprising a 5- or 6-nicotinyl-linker-carrier protein according to the invention and a pharmaceutically acceptable vehicle.

The vehicle in the pharmaceutical composition needed for administration of the immunogenic compound of the invention may be selected from known pharmaceutically acceptable vehicles, such as physiological saline solution or other suitable vehicle e.g. disclosed in the European or US Pharmacopoeia.

The pharmaceutical composition according to the invention may further comprise an adjuvant, which naturally must be pharmaceutically acceptable for human use, such as aluminum phosphate and aluminum hydroxide.

The invention is furthermore directed to a method of prophylactic and/or therapeutic immunological treatment of nicotine dependence from tobacco products to achieve harm reduction in an individual comprising administration of a 5- or 6-nicotinyl-linker-carrier protein having the formula

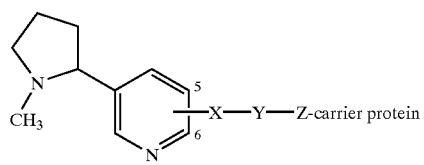

wherein

X is —NH—CO— or —NH— or —C≡C— or —CH=CH— or —CH$_2$—;

Y is —(CH$_2$)$_k$— or —(CH$_2$)$_m$—C$_6$H$_{10}$—(CH$_2$)$_n$— or —(CH$_2$)$_m$—C$_6$H$_4$—(CH$_2$)$_n$— wherein k=0–20, m=0–6, and n=0–6, when

Z is —NH—,
with the provisio that X is not —NH—CO— when Y is (CH$_2$)$_5$ and Z is —NH—, and X is —NH—CO— or —C≡C— or —CH=CH— or —CH$_2$—, Y is —(CH$_2$)$_m$—C$_6$H$_{10}$—(CH$_2$)$_n$— or —(CH$_2$)$_m$—C$_6$H$_4$—(CH$_2$)$_n$—
wherein m=0–6, and n=0–6, when Z is —CO—, and X is —C≡C— or —CH=CH—, Z is —CO—, when Y is —(CH$_2$)$_k$—
wherein k=0–20, to said individual in antibody-eliciting amounts for eliciting antibodies binding to nicotine molecules.

For a specific individual the antibody-eliciting amount will be found empirically by subjective experience of the stimulating effect in error and trial tests, or will be suggested by the manufacturer or physician.

In a preferred embodiment of this aspect of the invention the administration is repeated at intervals to enhance the titre of antibodies binding to nicotine molecules in said individual. The individual is preferably a human even though the invention would function if another mammal should be treated. This could of course be the case if laboratory animals were used for testing purposes.

The present invention will now be further illustrated by reference to the following description of drawings, synthesis of compounds and immunogens and experiments which describe specific embodiments of the invention. However, these are not to be considered as limitations to the scope of the invention defined in the claims.

DESCRIPTION OF THE DRAWINGS

FIG. 5. Electrophysiological single-cell recordings from VTA DA neurones in control rats. The DA cells responded with an increase in firing rate and burst firing after nicotine administration.

FIG. 7a. Active immunization using immunogen GK84-KLH essentially completely suppresses nicotine-induced dopamine release in nucleus accumbens shell compared to controls.

DESCRIPTION OF SYNTHESIS OF COMPOUNDS AND IMMUNOGENS

Figure 1:
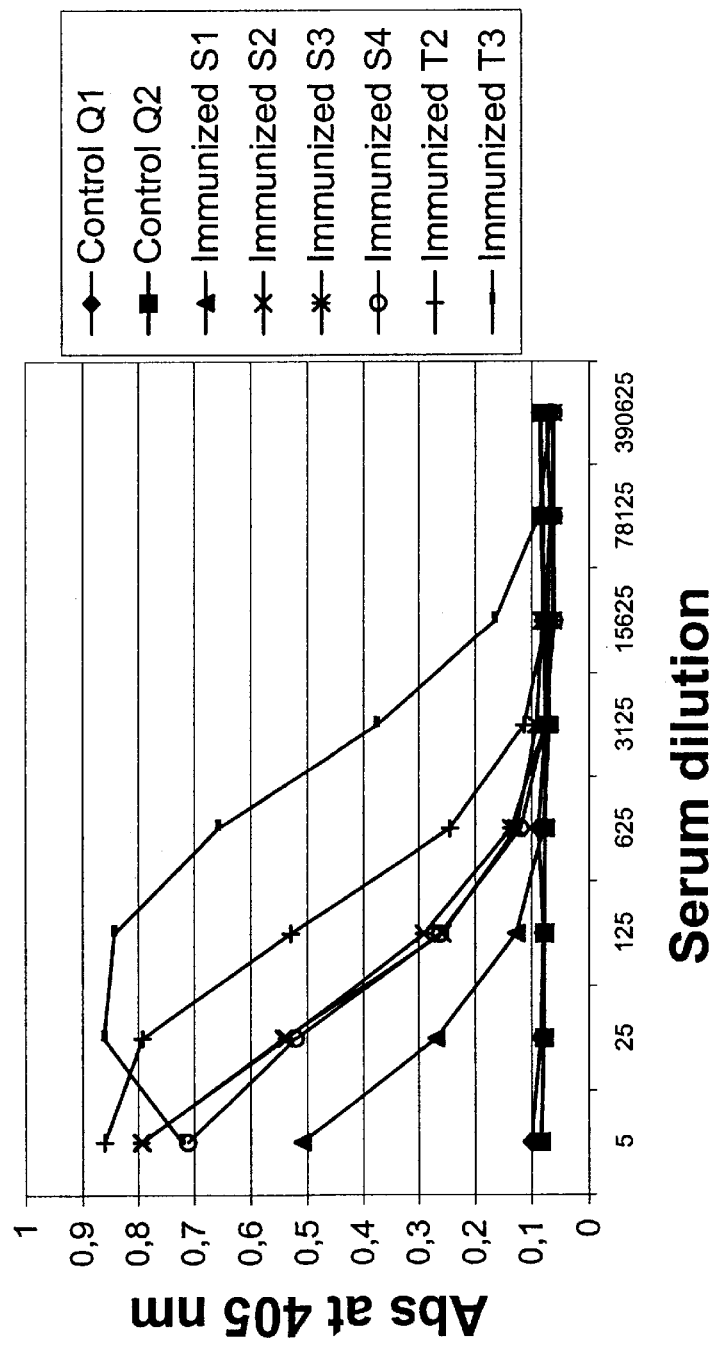
FIG. 1. Elisa measurements on serum from immunized rats collected 7 or 9 days after the first bolus immunization with GK5-KLH.

The nicotine immunogens were prepared in three steps according to Scheme 1:

I. preparation of 6-aminonicotine (1) from (S)-nicotine,
II. preparation of various nicotine-linker molecules,
III. preparation of various nicotine immunogens (nicotine-linker-carrier protein).

Experimental details of the three steps follow below:

I. Preparation of 6-Aminonicotine (1)

6-Aminonicotine (1) was synthesized from (S)-nicotine according to the procedure reported by Tschitschibabin and Kirssanow *Chem. Ber.* 1924, 57B, 1163–1168.

II. Preparation of Various Nicotine-linker Molecules (Schemes 2–8)

General Procedure for Coupling of 6- or 5-Aminonicotine With Amine Derivatives as Linkers (Schemes 2–3): N-Ethyldiisopropylamine (DIEA, 3.0 equiv) was added to a mixture of 6-aminonicotine (1.0 equiv), an amino protected amino acid [7-(tert-butyloxycarbonylamino)-heptanoic acid or trans-4-(benzyloxycarbonylaminomethyl)cyclohexanecarboxylic acid[1]] (1.0 equiv) and tripyrrolidinobromo-phosphonium hexafluorophosphate (PyBrOP, 1.0 equiv) in $CH_2Cl_2$ (1–2 mL/mmol). The reaction mixture was stirred at ambient temperature for 20–24 h. The mixture was concentrated and the residue was chromatographed to give the 6-acylated 6-aminonicotine derivatives 2 and 3 in 32–38% yield.

[1]Okano, A.; Inaoka, M.; Funabashi, S.; Iwamoto, M.; Isoda, S.; Moroi, R.; Abiko, Y.; Hivata, M. *J Med. Chem.* 1972, 15, 247–255.

7-(tert-Butyloxycarbonylamino)-N-[5-(1-methyl-2-pyrrolidinyl)-2-pyridinyl]heptan-amide (2). The residue was chromatographed [silica gel, $CHCl_3$/MeOH (30:1)] to give 2 (32%). An analytical sample was obtained by crystallization from iso-hexane/EtOH: mp 92–93° C.; $^1$H-NMR ($CDCl_3$, 270 MHz) δ 9.34, (br s, 1H), 8.16–8.11 (m, 2H), 7.63, (dd, J=8.5, 2.5 Hz, 1H), 4.68 (br s, 1H), 3.20–3.10 (m, 1H), 3.08–2.90 (m, 3H), 2.32 (t, J=7.5 Hz, 2H) 2.30–2.15 (m, 1H), 2.15–2.00 (m, 1H), 2.07 (s, 3H), 1.96–1.55 (m, 5H), 1.45–1.20 (m, 6H), 1.36 (s, 9H); $^{13}$C NMR ($CDCl_3$, 100 MHz) δ 171.9, 155.8, 150.9, 146.5, 137.5, 134.3, 114.2, 78.7, 68.4; 56.7, 40.3, 40.1, 37.2, 35.0, 28.7, 28.3, 26.3, 25.1, 22.3.

trans-4-(Benzyloxycarbonylaminomethyl)-N-[5-(1-methyl-2-pyrrolidinyl)-2-pyridinyl]cyclohexanecarboxamide (3). The residue was chromatographed [silica gel, EtOAc/MeOH (20:1)] to afford 3 (38%). An analytical sample was obtained by crystallization from iso-hexane/EtOH: mp 173–174° C.; $^1$H-NMR ($CD_3OD$, 400 MHz) δ 8.76 (s, 1H), 8.22–8.18 (m, 2H), 7.70 (dd, J=2, 8.5 Hz, 1H), 7.40–7.30 (m, 5H), 5.10 (s, 2H), 4.94–4.90 (m, 1H), 3.27–3.18 (m, 1H), 3.09–2.99 (m, 3H), 2.35–2.10 (m, 3H), 2.15 (s, 3H), 2.06–1.4 (m, 10H), 1.07–0.88 (m, 2H); $^{13}$C NMR ($CD_3OD$, 100 MHz) δ 174.4, 156.5, 150.8, 146.7, 137.6, 136.5, 134.6, 128.4 (2C's), 128.0 (3C's), 114.1, 68.5, 66.6, 56.9, 47.0, 46.1, 40.3, 37.5, 35.1, 29.6 (2C's), 28.8 (2C's), 22.4;

7-Amino-N-[5-(1-methyl-2-pyrrolidinyl)-2-pyridinyl] heptanamide (4:YH15). TFA (5 mL) was added to a solution of 2 (0.10 g, 0.25 mmol) in $CH_2Cl_2$ (20 mL) and the mixture was stirred at ambient temperature for 2 h. The solution was neutralized with saturated aqueous $K_2CO_3$ and extracted with $CH_2Cl_2$ (3×15 mL). The combined organic phases was washed with water, dried ($K_2CO_3$), filtered and concentrated. The crude product was purified by preparative TLC [silica gel, $CHCl_3$/MeOH/$NH_4OH$ (50:50:1)] to afford 0.06 g (74%) of 4 as an oil; $^1$H NMR ($CD_3OD$, 400 MHz) δ 8.21 (d, J=2 Hz, 1H), 8.07, (d, J=8.5 Hz, 1H), 7.74 (dd, J=8.5, 2.5 Hz, 1H), 3.23–3.17 (m, 1H), 3.13–3.08 (m, 1H), 2.65–2.60 (m, 2H), 2.42 (t, J=7.5 Hz, 2H), 2.36–2.28 (m, 1H), 2.23–2.16 (m, 1H), 2.14 (s, 3H), 2.00–1.66 (m, 5H), 1.52–1.33 (m, 6H); $^{13}$H NMR ($CD_3OD$, 100 MHz) δ 174.8, 152.5, 148.5, 138.5, 134.7, 115.5, 69.8, 57.8, 42.4, 40.5, 37.8, 35.3, 33.4, 30.1, 27.7, 26.6, 23.1;

trans-4-(Aminomethyl)-N-[5-(1-methyl-2-pyrrolidinyl)-2-pyridinyl]cyclohexanecarboxamide (5:YH6). A mixture of 3 (0.14 g, 0.3 mmol), $Me_3SiCl$ (0.24 g, 2.25 mmol) and NaI (4.5 mg, 2.7 mmol) in dry acetonitrile (10 mL) was stirred at ambient temperature for 3 h under nitrogen. The volatiles were evaporated and MeOH (5 mL) and a saturated solution of HCl in ether (1 mL) were added. The mixture was stirred for 15 min and then concentrated. The residue was diluted with water (5 mL) and extracted with EtOAc (3×7 mL). The combined organic phases was dried ($K_2CO_3$), filtered and concentrated. The crude product was purified by preparative TLC [silica gel, $CHCl_3$/MeOH/$NH_4OH$ (50:50:1)] to afford 0.03 g (28%) of 5; $^1$H-NMR ($CDCl_3$, 270 MHz) δ 8.83 (br s, 1H), 8.17–8.09 (m, 2H), 7.64 (dd, J=2, 8.5 Hz, 1H), 3.20–3.10 (m, 1H), 2.96 (t, J=8 Hz, 1H), 2.49 (br s, 2H), 2.08 (s, 3H), 2.28–1.18 (m, 15H), 0.94–0.84 (m, 2H); $^{13}$C NMR ($CDCl_3$, 68 MHz) δ 174.6, 150.9, 146.6, 137.6, 134.5, 114.1, 68.4, 56.8, 48.3, 46.3, 40.2, 35.1, 29.7 (2C's), 29.6, 28.9 (2C's), 22.4;

6-[5-(1-methyl-2-pyrrolidinyl)-2-pyridinyl]hexanenitrile (6). A stirred mixture of 6-aminonicotine (0.62 g, 3.5 mmol) and NaH (80% in mineral oil, 0.16 g, 5.25 mmol) in dry toluene (20 mL) was refluxed for 2 h and then cooled to room temperature. 6-Bromohexane-nitrile (0.65 g, 3.7 mmol) was added and the reaction was left at ambient temperature over night. The solvent was evaporated and the residue was chromatographed [silica gel, $CHCl_3$/MeOH/$NH_4OH$ (18:3:0.1)] to afford 0.40 g (41%) of 6; IR (film): 2270 $cm^{-3}$ (CN); $^1$H-NMR ($CDCl_3$, 270 MHz) δ 7.95 (d, J=2.5 Hz, 1H), 7.47 (dd, J=2.5, 8.5 Hz, 1H), 6.39 (d, J=8.5 Hz, 1H), 4.49 (m, 1H), 3.36–3.16 (m, 3H), 2.90 (t, J=9 Hz, 1H), 2.36 (t, J=7 Hz, 2H), 2.29–2.19 (m, 1H), 2.19–2.06 (m, 1H), 2.14 (s, 3H), 2.00–1.50 (m, 9H); $^{13}$C NMR ($CDCl_3$, 68 MHz) δ 158.2, 147.4, 136.5, 126.4, 119.4, 106.9, 68.5, 56.7, 41.7, 40.0, 34.3, 28.7, 26.0, 25.0, 22.1, 16.7;

6-[5-(1-methyl-2-pyrrolidinyl)-2-pyridinyl]hexanamine (7:YH7) Compound 6 (0.23 g, 0.83 mmol) was added to a suspension of $LiAlH_4$ (0.07 g, 2.5 mmol) in dry ether (8 mL) under nitrogen. The mixture was stirred at room temperature for 5 h, then heated under reflux for 20 h. Saturated aqueous $Na_2SO_4$ (2 mL) was added and the solid aluminum complex was filtered and washed with ether. The organic layer was dried ($K_2CO_3$), filtered and concentrated. The crude residue was purified by preparative TLC [silica gel, $CHCl_3$/MeOH/ $NH_4OH$ (35:35:2)] to afford 0.13 g (55%) of 7; $^1$H-NMR ($CD_3OD$, 400 MHz) δ 7.83 (d, J=2 Hz, 1H), 7.47 (dd, J=2, 9 Hz, 1H), 6.55, (d, J=9 Hz, 1H), 3.27 (t, J=7 Hz, 2H), 3.25–3.15 (m, 1H), 3.00–2.90 (m, 1H), 2.70 (br s, 2H), 2.35–2.26 (m, 1H) 2.21–2.09 (m, 1H), 2.16 (s, 3H), 2.10–1.74 (m, 3H), 1.69–1.35 (m, 8H); $^{13}$C NMR ($CD_3OD$, 100 MHz) δ 160.3, 147.8, 138.0, 125.5, 110.1, 70.2, 57.8, 42.8, 42.3, 40.5, 34.6, 33.0, 30.5, 28.2, 27.8, 22.9;

trans-Benzyl 4-[5-(1-methyl-2-pyrrolidinyl)-2-pyridinyl-carbamoyl]cyclohexane-carboxylate (8). DIEA (0.51 ml, 3 mmol) was added to a mixture of 6-aminonicotine (0.27 g, 1.5 mmol), 4-(benzyloxycarbonyl)cyclohexancarboxylic acid[2] (0.43 g, 1.6 mmol), and PyBrOP (0.77 g, 1.6 mmol) in $CHCl_3$ (20 ml). The reaction mixture was stirred at ambient temperature for 5 min and then heated under reflux for 24 h. Chloroform was evaporated in vacuo and the residue was extracted with ether. The combined ether extracts was washed with water followed by brine and then dried ($MgSO_4$), filtered and concentrated in vacuo. The residue was chromatographed [silica gel, $CH_2Cl_2$/MeOH (95:5)], to give 8 (0.44 g, 70%). An analytical sample was obtained by crystallization from iso-hexane; mp 116–118° C.; MS (EI, 20 eV) m/e 422 ($M^+$+1), 421 ($M^+$), 420 ($M^+$–H); $^1$H NMR ($CDCl_3$, 270 MHz) δ 8.61 (br s, 1H), 8.20–8.15 (m, 2H), 7.70 (dd, J=8.5, 2.5 Hz, 1H), 7.34 (m, 5H), 5.12 (s, 2H), 3.22 (m, 1H), 3.03 (app t, 1H), 2.45–1.40 (m, 15H), 2.16 (s, 3H); $^{13}$C NMR ($CDCl_3$, 68 MHz): δ 175.1, 174.1, 150.8, 146.8, 137.7, 136.0, 134.8, 128.5 (2C's), 128.1, 128.0 (2C's), 114.2, 68.5, 66.1, 56.9, 45.4, 42.3, 40.3, 35.1, 28.4 (2C's), 27.9 (2C's), 22.4;

[2]Wellmar, U. et al. *Nucleosides Nucleotides*, 1996, 15, 1059–1076.

trans-4-[5-(1-Methyl-2-pyrrolidinyl)-2-pyridinylcarbamoyl]cyclohexanecarboxylic acid (9:GK5). Palladium on carbon (10%, 0.04 g) was added to a mixture of 8 (0.15 g, 0.35 mmol) and cyclohexene (0.15 mL) in EtOH (7 mL). The stirred reaction mixture was heated under reflux for 15 min, filtered and concentrated. The residue was purified by preparative TLC (silica gel, MeOH), dissolved in $CH_2Cl_2$/EtOH (95:5), filtered and concentrated to yield 9 (0.09 g, 75%); MS (EI, 20 eV) m/e 332 ($M^+$+1), 331 ($M^+$), 330 ($M^+$–H); $^1$H NMR ($CDCl_3$, 270 MHz): δ 10.8 (br s, 1H), 8.34 (d, J=8.5 Hz, 1H), 8.06 (s, 1H), 7.79 (d, J=8.5 Hz, 1H), 3.23 (app t, 1H), 3.05 (app t, 1H), 2.60–1.50 (m, 15H), 2.12 (s, 3H); $^{13}$C NMR ($CDCl_3$+$CD_3OD$, 68 MHz): δ 179.6, 175.2, 151.0, 146.2, 138.1, 132.2, 114.4, 68.4, 56.3, 44.9, 42.7, 39.5, 33.7, 28.2, 28.0, 21.8;

7-(tert-Butyloxycarbonylamino)-N-[5-(1-methyl-2-pyrrolidinyl)-3-pyridinyl]heptan-amide (SG17). PyBrOP (0.9 g, 1.9 mmol) and DIEA (0.6 ml) was added to a stirred solution of 5-aminonicotine[3] (0.3 g, 1.7 mmol) and 7-(tert-butyloxycarbonylamino)heptanoic acid (0.5 g, 2.0 mmol) in dry $CH_2Cl_2$ (5 ml) at 0° C. The mixture was stirred at 0° C. for 30 min and then at room temperature for 2 h. The solvent was evaporated and EtOAc was added to the residue. The mixture was washed with aqueous saturated $NaHCO_3$ and brine, dried ($MgSO_4$), filtered and concentrated in vacuo. The residue was chromatographed [$SiO_2$, $CHCl_3$/MeOH (4:1)], to afford 0.59 g (87%) of SG17 as a light yellow oil; $^1$H-NMR (270 MHz, $CDCl_3$) δ 8.83 (br s, 1H), 8.59 (d, J=2 Hz, 1H), 8.27 (br s, 1H), 8.15 (br s, 1H), 4.75 (br s, 1H), 3.21 (ddd, J=9.5, 9.5, 2 Hz, 1H), 3.15–3.04 (m, 3H), 2.39–2.13 (m, 7H), 1.95–1.65 (m, 5H), 1.50–1.31 (m, 15H); $^{13}$C-NMR (68 MHz, $CDCl_3$) δ 172.5, 156.4, 144.4, 140.3, 139.2, 135.7, 126.4, 79.4, 68.9, 57.1, 40.5, 37.2, 35.2, 30.1, 28.6 (3Cs), 26.3, 25.5, 22.8;

[3]L. Rondahl. *Acta Pharm. Suec.* 1977, 14, 113–118.

7-Amino-N-[5-(1-methyl-2-pyrrolidinyl)-3-pyridinyl]heptanamide (SG18). TFA (2.0 ml, 26.0 mmol) was added to a stirred solution of SG17 (0.48 g, 1.2 mmol) in dry $CH_2Cl_2$ (35 ml) at 0° C. The stirred solution was allowed to reach room temperature and after 6 h the solution was brought to pH~8 by addition of aqueous saturated $K_2CO_3$. The mixture was evaporated to complete dryness under reduced pressure. The residue was chromatographed [$SiO_2$, $CHCl_3$MeOH/$NH_4OH$ (4:1:0.5] to afford 0.25 g (69%) of SG18 as a yellow oil; $^1$H-NMR (270 MHz, $CDCl_3$) δ 9.30 (br s, 1H), 8.59 (br s, 1H), 8.22–8.13 (m, 2H), 3.88 (br s, 2H), 3.16–3.12 (m, 1H), 3.08–3.02 (m, 1H), 2.71 (br s, 2H), 2.39–2.12 (m, 7H), 1.87–1.64 (m, 5H), 1.47–1.31 (m, 6H); $^{13}$C-NMR (68 MHz, $CDCl_3$) δ 172.7, 144.1, 140.0, 139.7, 135.9, 126.6, 68.8, 57.1, 41.5, 40.6, 37.1, 35.3, 31.9, 28.8, 26.4, 25.4, 22.8;

Preparation of Some Linkers (Scheme 4)

trans-(4-Prop-2-ynylcyclohexyl)methanol (GK91). Lithium acetylide ethylenediamine complex (7.4 g, 72.5 mmol) was suspended in 40 ml of dry DMSO and a solution of trans-4-(hydroxymethyl)cyclohexylmethyl toluene-4-sulfonate (8.0 g, 26.8 mmol) in DMSO (30 ml) was added at 5° C. The mixture was stirred for 2 h at ambient temperature, quenched with cold $H_2O$ (200 ml) and filtered through a pad of celite. The resulting solution was extracted with ether (4×50 ml). The combined organic layers was washed with water and brine, dried over $MgSO_4$, filtered and concentrated in vacuo yielding 3.5 g (86%) of GK91 which was used in the next step without further purification; $^1$H NMR ($CDCl_3$, 270 MHz) δ 3.44 (d, J=6 Hz, 2H), 2.10 (dd, J=6.5, 2.5 Hz, 2H) 1.97 (t, J=2.5 Hz, 1H), 1.86 (m, 4H), 1.72 (br s, 1H), 1.43 (m, 2H), 1.01 (m, 4H); $^{13}$C NMR ($CDCl_3$, 68 MHz) δ 83.3, 69.0, 68.4, 40.1, 37.1, 31.8, 29.1, 26.0. A portion of this material was converted to the 3,5-dinitrobenzoate. mp 106–108° C. (from iso-hexane); $^1$H NMR ($CDCl_3$, 270 MHz) δ 9.23 (t, J=2 Hz, 1H), 9.15 (d, J=2 Hz, 2H), 4.29 (d, J=6.5 Hz, 2H), 2.15 (dd, J=6.5, 2.5 Hz, 2H), 1.98 (t, J=2.5 Hz, 1H), 1.92 (m, 4H), 1.85 (m, 1H), 1.52 (m, 1H), 1.14 (m, 4H); $^{13}$C NMR ($CDCl_3$, 68 MHz) δ 162.5, 148.7, 134.1, 129.3, 122.3, 82.9, 71.7, 69.3, 36.9, 36.8, 31.4, 29.2, 25.9;

trans-4-Prop-2-ynylcyclohexanecarboxylic acid. (GK68). A solution of chromium trioxide (1.18 g, 11.8 mmol) in 2M $H_2SO_4$ (10 ml, 20 mmol) was maintained at 0° C. while 0.9 g (~5.9 mmol) of GK91 in acetone (20 ml) was added. The reaction mixture was stirred for 1 h at 0° C. and for 2 h at room temperature. The excess of oxidizing agent was destroyed with solid $Na_2SO_3$ (0.8 g, 6.3 mmol). Ether (~100 ml) was added and the mixture was extracted with brine (3×50 ml). The organic phase was dried ($Na_2SO_4$), filtered and concentrated. The residue was crystallized from iso-hexane to give 0.74 g (75%) of GK68 as colorless crystals. mp 84–86° C. (iso-hexane); $^1$H NMR ($CDCl_3$, 270 MHz) δ10.4 (br s, 1H), 2.27 (app tt, 1H), 2.12 (dd, J=6.5, 2.5 Hz, 2H), 1.98 (t, J=2.5 Hz, 1H), 2.15–1.87 (m, 4H), 1.6–1.35 (m, 3H), 1.09 (m, 2H); $^{13}$C NMR ($CDCl_3$, 68 MHz) δ182.4, 82.8, 69.4, 42.8, 36.2, 31.3, 28.4, 25.8;

trans-4-Prop-2-ynylcyclohexanecarboxylic acid methyl ester. (GK70). GK68 (0.7 g, 4.2 mmol) was dissolved in a mixture of MeOH (5 mL) and trimethyl orthoformate (1 mL).

Dowex 50W×X2 (0.2 g) was added and the reaction mixture was stirred overnight at ambient temperature. The resin was filtered off and the solvents were evaporated in vacuo. The residue was purified by bulb to bulb distillation (175° C., 13 mm) to give 0.71 g (93%) of GK70 as an oil; $^1$H NMR ($CDCl_3$, 270 MHz) δ 3.66 (s, 3H), 2.24 (app tt, 1H), 2.11 (dd, J=6.5, 2.5 Hz, 2H), 2.07–1.85 (m, 4H), 1.97 (t, J=2.5 Hz, 1H), 1.6–1.35 (m, 3H), 1.06 (m, 2H); $^{13}$C NMR ($CDCl_3$, 68 MHz) δ 176.3, 82.8, 69.3, 51.5, 43.0, 36.2, 31.4, 28.7, 25.8;

trans-(4-Prop-2-ynylcyclohexyl)methyl toluene-4-sulfonate(GK87). A solution of GK91 (3.04 g, 20 mmol) in pyridine (30 ml) was cooled to 0° C. and p-toluenesulfonyl chloride (4 g, 21 mmol) was added. The reaction mixture was stirred for 2 h at 0° C. and overnight at ambient temperature. The pyridine was evaporated in vacuo and the residue was dissolved in ether, washed with 1 M HCl, $H_2O$, NaHCO$_3$ and brine, dried over MgSO$_4$, filtered and evaporated. The solid residue was recrystallized from iso-hexane to give 5.57 g (91%) of GK87: mp 59–60° C.; $^1$H NMR (CDCl$_3$, 270 MHz) δ 7.78 (m, 2H), 7.34 (m, 2H), 3.82 (d, J=6.5 Hz, 2H), 2.45 (s, 3H), 2.07 (dd, J=6.5, 2.5 Hz, 2H), 1.95 (t, J=2.5 Hz, 1H), 1.80 (m, 4H), 1.60 (m, 1H), 1.41 (m, 1H), 0.97 (m, 4H); $^{13}$C NMR (CDCl$_3$, 68 MHz) δ144.6, 133.1, 129.8, 127.8, 82.9, 75.1, 69.2, 37.0, 36.7, 31.3, 28.7, 25.8, 21.6;

trans-(4-Prop-2-ynylcyclohexyl)methylamine (GK88). A solution of GK87 (1.53 g, 5 mmol) in MeOH (50 ml) was saturated with NH$_3$ at −15° C. and then heated in a sealed vessel at 100° C. for 3 h. The MeOH was evaporated in vacuo. The residue was dissolved in 1 M HCl (50 ml) and extracted with CH$_2$Cl$_2$ (3×20 ml) to remove bis(trans-(4-prop-2-ynyl-cyclohexylmethyl)amine hydrochloride. The water phase was alkalinized with solid NaOH to pH12 and extracted with ether (3×20 ml). The combined organic extracts were dried over KOH, filtered and concentrated in vacuo to give 0.4 g (53%) of GK88; $^1$H NMR (CDCl$_3$, 270 MHz) δ 2.51 (br d, 2H), 2.07 (m, 2H), 1.94 (m, 1H), 1.83 (m, 4H), 1.42 (m, 1H), 1.3–0.8 (m, 7H); $^{13}$C NMR (CDCl$_3$, 68 MHz) δ 83.3, 68.9, 48.6, 41.0, 37.2, 32.0, 30.3, 26.0;

6-Bromohexylammonium bromide[4] (SG20). A mixture of 6-amino-1-hexanol (4.3 g, 37.0 mmol) in HBr 48% (105 ml) was stirred at 95° C. for 11 h. The solution was concentrated in vacuo to afford 8.5 g (89%) of SG20 as a brownish hygroscopic powder (mp of crude SG20: 128–132° C.); $^1$H-NMR (270 MHz, CD$_3$COCD$_3$) δ 8.30 (br s, 2H), 3.53 (t, J=7 Hz, 1H), 3.52 (t, J=7 Hz, 1H), 3.13–3.06 (m, 2H), 1.91–1.87 (m, 4H), 1.54–1.46 (m, 4H); $^{13}$C-NMR (68 MHz) CD$_3$COCD$_3$) δ 40.5, 34.8, 33.4, 28.3, 27.7, 26.4;

[4]Dumont, J. L.; Chodkiewicz, W.; Cadiot, P. Bull. Soc. Chim. Fr. 1967, 2, 558–596.

7-Octynamine[5] (SG26). A solution of SG20 (3.0 g, 11.5 mmol) in dry DMSO (2 ml) was added dropwise over a period of 45 min to a stirred slurry of lithium acetylide, ethylendiamine complex (7.0 g, 76.0 mmol) in dry DMSO (36 ml) at 8° C. After 3 h at 8° C. the slurry was slowly poured into a cooled solution of brine (ca 300 ml). The solution was extracted with hexane (3×150 ml) and the combined organic phases was dried over Na$_2$SO$_4$, filtered and concentrated in vacuo at room temperature to afford 1.0 g (69%) of SG26 as a light yellow oil; IR (film) ν$_{max}$ 2114, 3296 cm$^{-1}$; $^1$H NMR (270 MHz, CDCl$_3$) δ 2.63 (t; J=7 Hz, 2H), 2.14 (dt; J=7, 2.5 Hz, 2H), 1.88 (t; J=2.5 Hz, 1H), 1.39–1.31 (m, 10H); $^{13}$C NMR (68 MHz, CDCl$_3$) δ 84.6, 68.3, 42.2, 33.7, 28.6, 28.5, 26.4, 18.4;

[5]Novis Smith, W. and Beumel, O. F. Synthesis, 1974, 441–442.

General procedure for coupling of 6-bromonicotine and 5-bromonicotine with terminal alkynes. (Scheme 5) A mixture of 6-bromonicotine[6] (or 5-bromonicotine[7]) (0.24 g, 1 mmol), bis(triphenyl-phosphine)palladium dichloride (0.014 g, 0.02mmol) and CuI (0.004 g, 0.02mmol) in 5 ml of Et$_3$N was deoxygenated with N$_2$. The acetylenic compound (1.1 mmol) was added and the reaction mixture was heated at 120° C. for 40 min (4 h for 5-bromonicotine) in a sealed vessel. The Et$_3$N was evaporated in vacuo and the residue was dissolved in EtOAc, washed with saturated aqueous NaHCO$_3$ and extracted with 20 ml of 2N HCl. The acidic aqueous phase was extracted with EtOAc (4×20 ml). The aqueous layer was saturated with solid NaHCO$_3$ and extracted with EtOAc (3×30 ml). The organic phase was washed with brine, dried (MgSO$_4$), filtered and concentrated in vacuo. The residue was purified by column chromatography.

[6]M. Dukat, W. Fiedler, D. Dumas, I. Damaj, B. R. Martin, J. A. Rosecrans, J. R. James, R. A. Glennon. Eur. J. Med. Chem. 1996, 31, 875–888. [7]L. S. Bleicher, N. D. P. Cosford, A. Herbaut, J. S. McCallum and I. A. McDonald. J.Org.Chem. 1998, 63, 1109–1118.

Methyl 4-[(5-(1-methyl-2-pyrrolidinyl)-2-pyridinyl)ethynyl]benzoate (GK47). Methyl 4-ethynylbenzoate was prepared according to ref 8. Purification: column chromatography [silica, acetone/iso-hexane (1:2)]; yield 78%; mp 102–104° C. (iso-hexane); $^1$H NMR (CDCl$_3$, 270 MHz) δ 8.56 (br s, 1H), 8.03 (dd, J=8.5, 1.5 Hz, 2H), 7.72 (app dt, 1H), 7.63 (dd, J=1.5 Hz, 2H), 7.52 (d, J=8 Hz, 1H), 3.92 (s, 3H), 3.25 (m, 1H), 3.13 (t, J=8 Hz, 1H), 2.4–2.1 (m, 5H), 2.1–1.6 (m, 3H); $^{13}$C NMR (CDCl$_3$, 68 MHz) δ 166.3, 149.9, 141.6, 138.9, 135.1, 131.8, 130.0, 129.4, 127.2, 127.0, 91.3, 87.7, 68.6, 56.9, 52.2, 40.3, 35.3, 22.6;

Methyl 7-(5-(1-Methyl-2-pyrrolidinyl)-2-pyridinyl)hept-6-ynoate. (GK79). Methyl 6-heptynoate was prepared according to ref 9. Purification: column chromatography [silica, acetone/iso-hexane (1:2)]; yield 73%; $^1$H NMR (CDCl$_3$, 270 MHz) δ 8.45 (d, J=2 Hz, 1H), 7.63 (dd, J=8, 2 Hz, 1H), 7.33 (d, J=8 Hz, 1H), 3.67 (s, 3H), 3.23 (m, 1H), 3.08 (app t, 1H), 2.47 (t, J=7 Hz, 2H), 2.37 (t, J=7 Hz, 2H), 2.31 (m, 1H), 2.18 (m, 1H), 2.16 (s, 3H), 2.05–1.6 (m, 7H); $^{13}$C NMR (CDCl$_3$, 68 MHz) δ173.7, 149.5, 142.5, 137.7, 134.9, 126.6, 89.6, 80.7, 68.6, 56.9, 51.4, 40.3, 35.1, 33.5, 27.7, 24.1, 22.5, 19.0; [9]E. C. Taylor et al. J. Org. Chem. 1991, 56, 1807–1812.

Methyl 7-(5-(1-Methyl-2-pyrrolidinyl)-3-pyridinyl)hept-6-ynoate. (GK77).). Methyl 6-heptynoate was prepared according to ref 9. Purification: column chromatography [silica, acetone/iso-hexane (1:2)]; yield 60%; $^1$H NMR (CDCl$_3$, 270 MHz) δ 8.51 (br s, 1H), 8.42 (br s, 1H), 7.71 (br s, 1H), 3.68 (s, 3H), 3.24 (m, 1H), 3.08 (app t, 1H), 2.46 (t, J=7 Hz, 2H), 2.38 (t, J=7 Hz, 2H), 2.31 (m, 1H), 2.20 (m, 1H), 2.17 (s, 3H), 2.1–1.55 (m, 7H); $^{13}$C NMR (CDCl$_3$, 68 MHz) δ 173.8, 151.0, 147.8, 138.2, 137.3, 120.8, 92.9, 77.9, 68.5, 56.9, 51.5, 40.3, 35.1, 33.5, 27.9, 24.1, 22.6, 19.1;

trans-4-[3-(5-(1-Methyl-2-pyrrolidinyl)-2-pyridinyl) prop-2-ynyl]cyclohexanecarboxylic acid methyl ester (GK78). Purification: column chromatography [silica, acetone/iso-hexane (1:2)]; yield 87%; $^1$H NMR (CDCl$_3$, 270 MHz) δ 8.46 (d, J=2 Hz, 1H), 7.63 (dd, J=8, 2 Hz, 1H), 7.34 (d, J=8 Hz, 1H), 3.66 (s, 3H), 3.24 (m, 1H), 3.08 (app t, 1H), 2.4–2.1 (m, 8H), 2.1–1.3 (m, 10H), 1.15 (m, 2H); $^{13}$C NMR (CDCl$_3$, 68 MHz) δ 176.3, 149.5, 142.6, 137.7, 134.9, 126.7, 88.7, 81.5, 68.6, 56.9, 51.5, 43.0, 40.3, 36.4, 35.1, 31.6, 28.7, 26.8, 22.6;

trans-4-[3-(5-(1-Methyl-2-pyrrolidinyl)-3-pyridinyl) prop-2-ynyl]cyclohexanecarboxylic acid methyl ester (GK75). Purification: column chromatography [silica, acetone/iso-hexane (1:2)]; yield 58%; $^1$H NMR (CDCl$_3$, 270 MHz) δ 8.50 (d, J=2 Hz, 1H), 8.41 (d, J=2 Hz, 1H), 7.71 (d, J=2 Hz, 1H), 3.67 (s, 3H), 3.25 (m, 1H), 3.08 (app t, 1H), 2.4–2.1 (m, 8H), 2.1–1.3 (m, 10H), 1.14 (m,2H); $^{13}$C NMR (CDCl$_3$, 68 MHz) δ 176.3, 151.1, 147.8, 138.1, 137.2, 120.8, 91.9, 78.6, 68.5, 56.9, 51.5, 43.0, 40.3, 36.5, 35.1, 31.6, 28.7, 26.9, 22.6;

2-(3-Hydroxy-3-methylbut-1-ynyl)-5-(1-methyl-2-pyrrolidinyl)pyridine (GK55). Purification: column chromatography [silica, acetone/iso-hexane (1:1)]; yield 90%; $^1$H NMR (CDCl$_3$, 270 MHz) δ 8.47 (d, J=2 Hz, 1H); 7.67 (dd, J=8, 2 Hz, 1H), 7.37 (d, J=8 Hz, 1H), 3.50 (br s, 1H) 3.23 (m, 1H), 3.08 (app t, 1H), 2.30 (m, 1H), 2.19 (m, 1H), 2.15 (s, 3H), 2.05–1.55 (m, 3H), 1.64 (s, 6H); $^{13}$C NMR (CDCl$_3$, 68 MHz) δ 149.4, 141.7, 138.3, 135.1, 127.0, 94.0, 81.2, 68.6, 65.0, 56.9, 40.3, 35.1, 31.2, 22.6;

trans-4-[3-(5-(1-Methyl-2-pyrrolidinyl)-3-pyridinyl)-prop-2-ynyl]cyclohexylmethyl-amine (GK89). Purification: column chromatography [silica, CHCl$_3$:MeOH saturated with NH$_3$ (15:1)]; yield 90%; $^1$H NMR (CDCl$_3$, 270 MHz)

δ 8.50 (d, J=2 Hz, 1H), 8.40 (d, J×2 Hz, 1H), 7.70 (t, J=2 Hz, 1H), 3.24 (m, 1H), 3.07 (app t, 1H), 2.55 (d, J=6.5 Hz, 2H), 2.33 (d, J=6.5 Hz, 2H), 2.17 (s, 3H), 2.4–2.1 (m, 2H), 2.1–1.4 (m, 10H), 1.26 (m, 1H), 1.2–0.85 (m, 4H); $^{13}$C NMR (CDCl$_3$, 68 MHz) δ 151.0, 147.7, 138.2, 137.2, 120.9, 92.4, 78.4, 68.4, 56.9, 48.5, 40.9, 40.3, 37.4, 35.1, 32.2, 30.3, 27.0, 22.6;

8-[5-(1-Methyl-2-pyrrolidinyl)-3-pyridinyl]oct-7-ynamine (SG29). The reaction mixture was heated for 6 h. Purification: column chromatography [SiO$_2$, CHCl$_3$/MeOH/ NH$_4$OH, (5:1:0.1)]; yield 0.36 g (86%) (based on recovered 5-bromonicotine); IR (film) v$_{max}$ 2232 cm$^{-1}$; $^1$H-NMR (270 MHz, CDCl$_3$) δ 8.47 (d, J=2 Hz, 1H), 8.38 (d, J=2 Hz, 1H), 7.68 (dd, J=2, 2 Hz, 1H), 3.21 (ddd, J=9.5, 9.5, 2 Hz 1H), 3.08–3.01 (m, 1H), 2.71–2.66 (m, 2H), 2.40 (t, J=7 Hz, 2H), 2.34–2.11 (m, 5H), 1.98–1.31 (m, 13H); $^{13}$C-NMR (68 MHz, CDCl$_3$) δ 147.2, 143.9, 134.5, 133.5, 117.1, 89.7, 64.7, 53.1, 37.8, 36.6, 31.3, 28.7, 24.8, 24.6, 22.5, 18.8, 15.5;

trans-4-[3-(5-(1-Methyl-2-pyrrolidinyl)-2-pyridinyl)-prop-2-ynyl]-cyclohexylmethylamine (GK90). A mixture of 6-bromonicotine (0.47g, 2 mmol), tris(dibenzylideneacetone)-dipalladium [(dba)$_3$Pd$_2$] (0.018 g, 0.02 mmol), 1,3-bis(diphenylphosphino)propane (dppp) (0.032 g, 0.08 mmol) and CuI (0.008 g, 0.04 mmol) in 15 ml of Et$_3$N was deoxygenated with N$_2$ and then GK88 (0.326 g, 2.16 mmol) was added. The reaction mixture was heated at 120° C. for 6 h in a sealed vessel. The Et$_3$N was evaporated in vacuo. The residue was dissolved in EtOAc, washed with diluted NaOH solution and extracted with 40 ml of 2N HCl. The acidic aqueous phase was extracted with EtOAc (4×20 ml). The aqueous layer was alkalinized with solid NaOH to pH12 and extracted with EtOAc (5×30 ml). The combined organic phases was washed with brine, dried (MgSO$_4$), filtered and concentrated in vacuo. The residue was purified by column chromatography [silica, CHCl$_3$/MeOH saturated with NH$_3$, (15:1)] yielding 0.43 g (71%) of GK90; $^1$H NMR (CDCl$_3$, 270 MHz) δ 8.46 (d, J=2 Hz, 1H), 7.62 (dd, J=8, 2 Hz, 1H), 7.34 (d, J=8 Hz, 1H), 3.23 (m, 1H), 3.07 (app t, 1H) 2.53 (d, J=6.5 Hz, 2H), 2.34 (d, J=6.5 Hz, 2H), 2.30 (app q, 1H), 2.18 (m, 1H), 2.15 (s, 3H), 2.05–1.45 (m, 8H), 1.35–0.85 (m, 7H); $^{13}$C NMR (CDCl$_3$, 68 MHz) δ 149.5, 142.7, 137.6, 134.8, 126.7, 89.3, 81.3, 68.6, 56.9, 48.7, 41.0, 40.3, 37.4, 35.1, 32.3, 30.3, 26.9, 22.6;

trans-3-(5-(1-Methyl-2-pyrrolidinyl)-3-pyridinyl)acrylic acid methyl ester (GK59). A mixture of 5-bromonicotine (0.241 g, 1 mmol), Pd(OAc)$_2$ (0.011 g, 0.05 mmol), tri-o-tolylphosphine (0.060 g, 0.2 mmol) and Et$_3$N (0.17 ml, 1.25 mmol) in 5 ml of MeCN was deoxygenated with N$_2$ and methyl acrylate (0.112 ml, 1.25 mmol) was added. The reaction mixture was heated in a sealed vessel at 110° C. overnight. MeCN was evaporated in vacuo and the residue was dissolved in EtOAc, washed with saturated NaHCO$_3$ solution and extracted with 20 ml of 2N HCl. The acidic aqueous phase was extracted with EtOAc (4×20 ml). The aqueous layer was saturated with solid NaHCO$_3$ and extracted with EtOAc (3×30 ml). The organic phase was washed with brine, dried (MgSO$_4$), filtered and concentrated in vacuo. The residue was purified by column chromatography [silica, CHCl$_3$/MeOH, (40:1)]; yield 0.2 g (80%); mp 4244° C.; $^1$H NMR (CDCl$_3$, 270 MHz) δ 8.62 (d, J=2 Hz, 1H), 8.53 (d, J=2 Hz, 1H), 7.87 (t, J=2 Hz, 1H), 7.69 (d, J=16.0 Hz, 1H), 6.55 (d, J=16.0 Hz, 1H), 3.82 (s, 3H), 3.26 (m, 1H), 3.15 (app t, 1H), 2.34 (app q, 1H), 2.22 (m, 1H), 2.18 (s, 3H), 2.1–1.6 (m, 3H); $^{13}$C NMR (CDCl$_3$, 68 MHz) δ 166.7, 150.9, 148.6, 141.2, 139.3, 132.8, 130.1, 119.9, 68.4, 56.9, 51.8, 40.4, 35.3, 22.6;

Methyl 4-[(5-(1-methyl-2-pyrrolidinyl)-3-pyridinyl)ethynyl]benzoate (YH19). A mixture of 5-bromonicotine (0.44 g, 1.82 mmol), Pd(OAc)$_2$ (60 mg, 0.34 mmol), Ph$_3$P (0.19 g, 0.72 mmol), CuI (30 mg) and Et$_3$N (30 mL) was stirred at room temperature for 30 min. Methyl 4-ethynylbenzoate[8] (0.32 g, 2 mmol) was added and the mixture was refluxed over night. The reaction mixture was allowed to reach room temperature, diluted with CH$_2$Cl$_2$ (120 mL) and washed with H$_2$O. The organic phase was dried (MgSO$_4$), filtered and concentrated. The residue was chromatographed [SiO$_2$, CHCl$_3$/MeOH (50:1)] to give 0.37 g (64%) of YH19. An analytical sample was recrystallized from EtOH/iso-hexane; mp: 97–98° C.; $^1$H NMR (270 MHz, CDCl$_3$) δ 8.65 (br s, 1H), 8.49 (br s, 1H), 8.03–7.97 (m, 2H), 7.85 (br s, 1H), 7.59–7.53 (m, 2H), 3.89 (s, 3H), 3.27–3.19 (m, 1H), 3.10 (t, J=8.5 Hz, 1H), 2.36–2.13 (m, 2H), 2.17 (s, 3H), 2.04–1.62 (m, 3H); $^{13}$C NMR (270 MHz, CDCl$_3$) δ 166.3, 150.9, 148.8, 138.6, 137.4, 131.5, 129.8, 129.5, 127.2, 119.7, 91.5, 89.0, 68.3, 56.9, 52.2, 40.3, 35.2, 22.7;

[8]S. J. Havens and P. M. Hergenrother. *J. Org. Chem.* 1985, 50, 1763–1765.

General Procedure for the Hydrolysis of Esters (Scheme 6).

4-[(5-(1-Methyl-2-pyrrolidinyl)-2-pyridinyl)ethynyl] benzoic acid (GK49). A mixture of GK47 (0.185 g, 0.58 mmol) and KOH (0.097 g, 1.73 mmol) in 50% aqueous MeOH (10 ml) was heated under reflux for 30 min. The reaction mixture was acidified with HOAc to pH 8 and the solvents were evaporated in vacuo. The crude product was purified by column chromatography (silica gel, CHCl$_3$/MeOH, gradient of MeOH 10% to 50%). The solvents were evaporated in vacuo. The residue was dissolved in CH$_2$Cl$_2$/EtOH, (95:5), filtered and evaporated in vacuo to give 0.17 g (96%) of GK49; $^1$H NMR (CD$_3$OD, 270 MHz) δ 8.54 (br s, 1H), 8.04 (d, J=8.5 Hz, 2H), 7.91 (dd, J=8, 2 Hz, 2H), 7.64 (d, J=8 Hz, 1H), 7.60 (d, J=8.5 Hz, 2H), 3.46 (app t, 1H), 3.36 (m, 1H), 2.55 (app q, 1H), 2.40–2.20 (m, 4H), 2.10–1.80 (m, 3H); $^{13}$C NMR (CD$_3$OD, 68 MHz) δ 174.1, 150.8, 143.5, 138.4, 138.2, 137.9, 132.6, 130.8, 128.9, 125.6, 90.7, 90.2, 70.1, 57.9, 40.5, 35.2, 23.4;

7-(5-(1-Methyl-2-pyrrolidinyl)-2-pyridinyl)hept-6-ynoic acid (GK81). The compound was purified by preparative TLC [silica, CHCl$_3$/MeOH, (5:1)]; yield 93%; $^1$H NMR (CDCl$_3$, 270 MHz) δ 11.49 (br s, 1H), 8.40 (br s, 1H), 8.68 (dd, J=8, 2 Hz, 1H), 7.31 (d, J=8 Hz, 1H), 3.32 (m, 1H), 3.22 (app t, 1H), 2.5–2.1 (m, 9H), 2.1–1.5 (m, 7H); $^{13}$C NMR (CDCl$_3$, 68 MHz) δ 177.1, 149.3, 142.8, 135.6, 135.3, 126.9, 91.1, 80.0, 68.7, 56.3, 39.6, 34.2, 33.9, 27.8, 24.4, 22.1, 19.1;

7-(5-(1-Methyl-2-pyrrolidinyl)-3-pyridinyl)hept-6-ynoic acid (GK80). The compound was purified by preparative TLC [silica, CHCl$_3$/MeOH, (5:1)]; yield 79%; $^1$H NMR (CDCl$_3$, 270 MHz) δ 12.5 (br s, 1H), 8.47 (br s, 1H), 8.35 (br s, 1H), 7.75 (s, 1H), 3.30 (m, 1H), 3.18 (app t, 1H), 2.5–2.1 (m, 9H), 2.1–1.5 (m, 7H); $^{13}$C NMR (CDCl$_3$, 68 MHz) δ 176.8, 150.7 138.2, 136.5, 121.3, 93.9, 77.3, 68.5, 56.3, 39.7, 34.1 (2C's), 28.0, 24.4, 22.2, 19.2;

trans-4-[3-(5-(1-Methyl-2-pyrrolidinyl)-2-pyridinyl) prop-2-ynyl]cyclohexanecarboxylic acid (GK83). The compound was purified by column chromatography [silica, CHCl$_3$/MeOH, (10:1)]; yield 80%; $^1$H NMR (CDCl$_3$, 270 MHz) δ 10.2 (br s, 1H), 8.59 (s, 1H), 7.81 (d, J=8 Hz, 1H), 7.38 (d, J=8 Hz, 1H), 3.33 (m, 1H), 3.23 (m, 1H), 2.5–1.2 (m, 20H); $^{13}$C NMR (CDCl$_3$, 68 MHz) δ 179.4, 148.7, 141.9, 136.9 (br), 136.0, 127.0, 90.6, 80.6, 68.6, 56.7, 43.1, 40.0, 36.2, 34.6, 31.1, 29.1, 26.7, 22.5;

trans-4-[3-(5-(1-Methyl-2-pyrrolidinyl)-3-pyridinyl) prop-2-ynyl]cyclohexanecarboxylic acid (GK82). The compound was purified by preparative TLC [silica, CHCl$_3$/ MeOH, (10:1)]; yield 85%; $^1$H NMR (CD$_3$OD, 270 MHz) δ

8.48 (br s, 1H), 8.44 (br s, 1H), 7.90 (s, 1H), 3.50 (app t, 1H), 3.40 (m, 1H), 2.60 (app q, 1H), 2.4–1.8 (m, 14H), 1.65–1.35 (m, 3H), 1.18 (m, 2H); $^{13}$C NMR (CD$_3$OD, 68 MHz) δ 181.1, 152.2, 148.7, 139.7, 137.7, 123.2, 94.5, 79.0, 70.1, 57.8, 45.3, 40.3, 38.3, 35.0, 33.1, 30.5, 27.7, 23.3;

trans-4-[3-(5-(1-Methyl-2-pyrrolidinyl)-3-pyridinyl) propyl]cyclohexanecarboxylic acid (GK95). The compound was purified by preparative TLC [silica, CHCl$_3$/MeOH, (10:1)]; yield 93%; $^1$H NMR (CDCl$_3$+C$_6$D$_6$, 270 MHz) δ 11.89 (br s, 1H), 8.34 (d, J=2 Hz, 1H), 8.32 (d, J=2 Hz, 1H), 7.63 (app t, 1H), 3.28 (m, 1H), 2.97 (m, 1H), 2.44 (t, J=8 Hz, 2H), 2.35–1.35 (m, 14H), 2.05 (s, 3H), 1.15 (m, 3H), 0.85 (m, 2H); $^{13}$C NMR (CDCl$_3$+C$_6$D$_6$, 68 MHz) δ 179.3, 148.5, 146.5, 138.3, 136.6, 135.0, 68.6, 56.2, 43.9, 39.5, 37.0, 36.8, 34.1, 33.2, 32.4, 32.3, 29.2, 28.3, 22.0;

trans-3-(5-(1-Methyl-2-pyrrolidinyl)-3-pyridinyl)acrylic acid (GK62). The compound was purified by column chromatography [silica, CHCl$_3$/EtOH, (1:1)]; yield 82%; $^1$H NMR (CDCl$_3$, 270 MHz) δ 13.48 (br s, 1H), 8.73 (s, 1H), 8.47 (s, 1H), 8.40 (s, 1H), 7.64 (d, J=16 Hz, 1H), 6.76 (d, J=16 Hz, 1H), 3.83 (m, 1H), 3.55 (m, 1H), 2.62 (m, 1H), 2.5–2.0 (m, 7H); $^{13}$C NMR (CDCl$_3$, 68 MHz) δ 169.9, 149.8, 148.8, 138.1, 134.4, 134.0, 131.7, 125.3, 69.0, 55.6, 38.9, 33.4, 21.9;

4-[(5-(1-Methyl-2-pyrrolidinyl)-3-pyridinyl)ethynyl] benzoic acid (YH20). KOH (168 mg, 3 mmol) was added to YH19 (0.32 g, 1 mmol) in MeOH (5 mL). The stirred mixture was refluxed for 2 h and then cooled to room temperature. HOAc was added to pH8 and the volatiles were evaporated. The residue was chromatographed [SiO$_2$, CHCl$_3$/MeOH (5:1)] to give 0.19 g (62%) of YH$_{20}$; $^1$H NMR (270 MHz, CDCl$_3$) δ 11.00 (br s, OH), 8.75 (br s, 1H), 8.44 (m, 2H), 8.10 (d, J=8 Hz, 2H), 7.42 (d, J=8.5 Hz, 2H), 3.94–3.84 (m, 1H), 3.63–3.52 (m, 1H), 2.69–2.58 (m, 1H), 2.42 (s, 3H), 2.42–1.98 (m, 4H); $^{13}$C NMR (270 MHz, CDCl$_3$) δ 169.5, 151.6, 148.9, 139.0, 133.8, 132.9, 131.5, 129.6, 125.3, 120.8, 93.0, 87.4, 69.0, 55.5, 38.8, 33.2, 21.7;

4-(3-(N-Methylpyrrolidin-2-yl)pyridin-5-ylethyl)benzoic acid (YH24). KOH (130 mg, 2.32 mmol) was added to a solution of YH22 (0.12 g, 0.37 mmol), H$_2$O (3 mL) and 1,4-dioxane (3 mL). After reflux for 2 h the pH of the mixture was adjusted to 8 by addition of HOAc. Volatiles were evaporated and the residue was chromatographed [SiO$_2$, CHCl$_3$/MeOH (2:1)] to give 70 mg (61%) of YH24; $^1$H NMR (400 MHz, CDCl$_3$) δ 8.44 (br s, 2H), 7.92 (s, 1H), 7.88 (d, J=8 Hz, 2H), 7.12 (d, J=8 Hz, 2H), 3.98–3.91 (m, 1H), 3.75–3.66 (m, 1H), 2.99–2.85 (m, 5H), 2.50 (s, 3H), 2.43–2.31 (m, 1H), 2.27–2.06 (m, 3H); $^{13}$C NMR (400 MHz, CDCl$_3$) δ 172.9, 151.0, 148.4, 145.9, 139.6, 137.9, 134.1, 130.8 (2C's), 129.5 (3C's), 70.6, 57.2, 39.5, 38.2, 35.4, 33.7, 22.9;

General Procedure for Hydrogenation of Triple Bonds (Scheme 7).

trans-4-[3-(5-(1-Methyl-2-pyrrolidinyl)-2-pyridinyl) propyl]cyclohexanecarboxylic acid (GK84). GK83 (0.153 g, 0.47 mmol) in 40 ml of EtOH was hydrogenated at room temperature and atmospheric pressure over 0.1 g of 10% palladium on carbon for 1 h. The catalyst was filtered off and washed with EtOH. The solvent was evaporated in vacuo and the residue was purified by preparative TLC [silica, CHCl$_3$/MeOH, (10:1)] to give 0.07 g (45%) of GK84; $^1$H NMR (CD$_3$OD, 270 MHz) δ 8.55 (d, J=2 Hz, 1H), 7.96 (dd, J=8, 2 Hz, 1H), 7.42 (d, J=8 Hz, 1H), 4.14 (m, 1H), 3.69 (m, 1H), 3.08 (m, 1H), 2.81 (t, J=7.5 Hz, 2H), 2.61 (s, 3H), 2.47 (m, 1H), 2.21 (m, 4H), 2.0–1.6 (m, 6H), 1.5–1.1 (m, 5H), 0.96 (m, 2H); (CDCl$_3$, 68 MHz) δ 180.0, 163.3, 148.8, 136.8, 128.6, 123.7, 69.5, 55.8, 43.6, 38.4, 37.6, 32.3, 32.2, 29.1, 27.0, 21.5;

trans-4-[3-(5-(1-Methyl-2-pyrrolidinyl)-3-pyridinyl)-propyl]cyclohexylmethylamine (GK93). Purification: column chromatography [alumina, CHCl$_3$/MeOH, gradient of methanol 10–50%]; yield 78%; $^1$H NMR (270 MHz, CDCl$_3$) δ 8.34 (d, J=2 Hz, 1H), 8.32 (d, J=2 Hz, 1H), 7.50 (t, J=2 Hz, 1H), 3.25 (m, 1H), 3.06 (app t, 1H), 2.58 (t, J=7.5 Hz, 2H), 2.51 (d, J=6.5 Hz, 2H), 2.30 (app q, 1H), 2.19 (m, 1H), 2.17 (s, 3H), 2.05–1.55 (m, 9H), 1.32 (br s, 2H), 1.22 (m, 4H), 0.88 (m, 4H); $^{13}$C NMR (CDCl$_3$, 68 MHz) δ 148.8, 147.0, 138.0, 137.8, 134.3, 68.8, 56.9, 48.8, 41.3, 40.3, 37.6, 36.9, 35.1, 33.2, 32.7, 30.6, 28.5, 22.5;

trans-4-[3-(5-(1-Methyl-2-pyrrolidinyl)-3-pyridinyl) propyl]cyclohexanecarboxylic acid methyl ester (GK94). Purification: column chromatography [silica, acetone/isohexane (1:2)]; yield 79%; $^1$H NMR (CDCl$_3$, 270 MHz) δ 8.34 (d, J=2 Hz, 1H), 8.31 (d, J=2 Hz, 1H), 7.50 (d, J=2 Hz, 1H), 3.65 (s, 3H), 3.25 (m, 1H), 3.06 (app t, 1H), 2.58 (t, J=8 Hz, 2H), 2.4–2.1 (m, 3H), 2.17 (s, 3H), 2.05–1.55 (m, 9H), 1.40 (m, 2H), 1.24 (m, 3H), 0.91 (m, 2H); $^{13}$C NMR (CDCl$_3$, 68 MHz) δ 176.5, 148.8, 147.1, 138.1, 137.7, 134.3, 68.8, 57.0, 51.4, 43.3, 40.4, 36.7, 35.1, 33.2, 32.2, 28.9, 28.4, 22.5;

trans-4-[3-(5-(1-Methyl-2-pyrrolidinyl)-2-pyridinyl)-propyl]cyclohexylmethylamine (GK96). Purification: preparative TLC [silica, CHCl$_3$/MeOH saturated with NH$_3$ (15:1)]; yield 81%; $^1$H NMR (CDCl$_3$, 270 MHz) δ 8.41 (d, J=2 Hz, 1H), 7.60 (dd, J=8, 2 Hz, 1H), 7.11 (d, J=2 Hz, 1H), 3.23 (m, 1H), 3.04 (app t, 1H), 2.74 (t, J=8 Hz, 2H), 2.51 (d, J=6.5 Hz, 2H), 2.29 (app q, 1H), 2.19 (m, 1H), 2.16 (s, 3H), 2.05–1.65 (m, 9H), 1.49 (br s, 2H), 1.35–1.10 (m, 4H), 0.88 (m, 4H); $^{13}$C NMR (CDCl$_3$, 68 MHz) δ 161.4, 148.8, 135.5, 135.1, 122.5, 68.6, 57.0, 48.8, 41.4, 40.3, 38.4, 37.8, 37.1, 35.0, 32.8, 30.6, 27.4, 22.5;

8-[5-(1-Methyl-2-pyrrolidinyl)-3-pyridinyl]octanamine (SG30). A solution of SG29 (0.2 g, 0.7 mmol) in MeOH (20 ml) was hydrogenated at room temperature and at atmospheric pressure over 10% Pd/C (0.1 g). After 15 min the catalyst was filtered off and washed with MeOH. The volatiles was evaporated under reduced pressure and the residue was chromatographed [SiO$_2$, CHCl$_3$/MeOH/NH$_4$OH, (5:1:0.1)] to afford 0.16 g (76%) of SG30 as a colorless oil. $^1$H NMR (270 MHz, CDCl$_3$) δ 8.30 (d, J=2 Hz, 1H), 8.28 (d, J=2 Hz, 1H), 7.47 (brs, 1H), 3.21 (ddd, J=9.5, 9.5, 1.5 Hz, 1H), 2.99–3.05 (m, 1H), 2.64 (t, J=7 Hz, 2H), 2.56 (br t, J=8 Hz, 2H), 2.27 (dd, J=17.5, 9 Hz, 1H), 2.09–2.18 (m, 4H), 1.55–1.94 (m, 7H), 1.27–1.42 (m, 10H); $^{13}$C-NMR (68 MHz, CDCl$_3$) δ 149.0, 147.1, 138.2, 138.1, 134.6, 69.0, 57.2, 42.3, 40.6, 35.3, 33.8, 33.1, 31.3, 29.5, 29.3, 27.0, 22.7;

4-[2-(5-(1-Methyl-2-pyrrolidinyl)-2-pyridinyl)ethyl] benzoic acid (GK54). GK49 (0.09 g, 0.29 mmol) in 20 ml of MeOH was hydrogenated at room temperature and atmospheric pressure over 0.03 g of 10% palladium on carbon for 6 h. The catalyst was filtered off and washed with MeOH. The solvent was evaporated in vacuo and the residue was purified by silica gel chromatography [CHCl₃/MeOH, (5:1)] to give 0.052 g (57%) of GK54; $^1$H NMR (CD₃OD, 270 MHz) δ 8.52 (d, J=2 Hz, 1H), 7.88 (d, J=8.5 Hz, 2H), 7.83 (dd, J=8, 2 Hz, 1H), 7.25 (d, J=8 Hz, 1H), 7.19 (d, J=8.5 Hz, 2H), 3.74 (m, 1H), 3.51 (m, 1H), 3.08 (m, 4H), 2.76 (m, 1H), 2.41 (s, 3H), 2.36 (m, 1H), 2.07 (m, 3H); $^{13}$C NMR (CD₃OD, 68 MHz) δ 174.2, 162.7, 150.0, 146.1, 138.2, 134.5, 133.1, 130.8, 129.3, 125.1, 70.4, 57.5, 40.2, 39.8, 37.0, 33.9, 23.0;

Methyl 4-(3-(N-methylpyrrolidin-2-yl)pyridin-5-ylethyl) benzoate (YH22). A mixture of YH19 (0.15 g, 0.468 mmol) and Pd(C) (10%, 20 mg) in MeOH (10 mL) was hydrogenated at atmospheric pressure and room temperature for one day. The catalyst was removed by filtration through Celite and the filtrate was concentrated. The residue was chromatographed [SiO₂, CHCl₃/MeOH (60:1)] to give 0.15 g (95%) of YH22; $^1$H NMR (400 MHz, CDCl₃) δ 8.38 (br s, 2H), 7.91–7.80 (m, 2H), 7.40 (s, 1H), 7.16–7.14 (m, 2H), 3.85 (s, 3H), 3.23–3.16 (m, 1H), 3.05–2.87 (m, 5H), 2.30–2.22 (m, 1H), 2.18–2.08 (m, 1H), 2.09 (s, 3H), 1.92–1.84 (m, 1H), 1.81–1.72 (m, 1H), 1.67–1.57 (m, 1H); $^{13}$C NMR (400 MHz, CDCl₃) δ 166.9, 148.6, 147.3, 146.2, 138.3, 136.5, 134.5, 129.7, 128.0, 68.6, 56.9, 51.9, 40.2, 37.4, 35.0, 34.4, 22.4;

2-Ethynyl-5-(1-methyl-2-pyrrolidinyl)pyridine (GK58). GK55 (0.3 g, 1.23 mmol) and NaH as a 60% dispersion in mineral oil (0.01 g, 0.17 mmol) were dissolved in dry toluene (50 ml). The stirred solution was slowly distilled until the boiling point of the distillate reached 110° C. (approx. 25 ml of distillate collected). The rest of the toluene was evaporated in vacuo. The residue was chromatographed [SiO₂, CHCl₃/MeOH, (10:1)] to give 0.2 g, (87%) of GK58 as a brown oil; $^1$H NMR (CDCl₃, 270 MHz) δ 8.51 (d, J=2 Hz, 1H), 7.68 (dd, J=8, 2 Hz, 1H), 7.45 (d, J=8 Hz, 1H), 3.24 (m, 1H), 3.14 (s, 1H), 3.11 (app t, 1H), 2.32 (app q, 1H), 2.20 (m, 1H), 2.16 (s, 3H), 2.05–1.62 (m, 3H); $^{13}$C NMR (CDCl₃, 68 MHz) δ 149.7, 141.0, 139.1, 135.0, 127.3, 82.8, 76.6, 68.5, 56.9, 40.3, 35.2, 22.6;

Synthesis of GK56 and GK60 (Scheme 8).

5-(1-Methyl-2-pyrrolidinyl)-2-pyridinylpropiolic acid (GK60). A solution of GK58 (0.175 g, 0.94 mmol) in THF (20 ml) was cooled to −78° C. and BuLi (1.6M solution in hexane, 0.62 ml, 0.99 mmol) was added. The reaction mixture was stirred for 0.5 h at −78° C. and then CO₂ gas was added. After an additional 1 h at −78° C. the reaction mixture was allowed to warm to room temperature. THF was evaporated in vacuo and the residue was purified by preparative TLC [silica gel, CHCl₃/MeOH, (1:1)]; yield 0.20 g, (90%); $^1$H NMR (CD₃OD, 270 MHz) δ 8.49 (dd, J=2, 0.5 Hz, 1H), 7.85 (dd, J=8, 2 Hz, 1H), 7.59 (dd, J=8, 0.5 Hz, 1H), 3.34–3.21 (m, 2H), 2.42 (app q, 1H), 2.29 (m, 1H), 2.20 (s, 3H), 2.05–1.70 (m, 3H); $^{13}$C NMR (CD₃OD, 68 MHz) δ 160.4, 150.6, 142.5, 139.8, 137.7, 129.2, 87.4, 78.0, 70.0, 58.0, 40.7, 35.7, 23.5;

5-(1-Methyl-2-pyrrolidinyl)-3-pyridinylpropiolic acid (GK56) The compound was synthesized from 3-ethynyl-5-(1-methyl-2-pyrrolidinyl)pyridine[7] following the method described for the synthesis of GK60 to give GK56 in a 80% yield after purification by preparative TLC [silica gel, CHCl₃/MeOH, (1:1)]; $^1$H NMR (CD₃OD, 270 MHz) δ 8.56 (br s, 1H), 8.50 (br s, 1H), 7.93 (t, J=2 Hz, 1H), 3.22 (m, 2H), 2.38 (app q, 1H), 2.26 (m, 1H), 2.18 (s, 3H), 2.10–1.6 (m, 3H); $^{13}$C NMR (CD₃OD, 68 MHz) δ 160.7, 152.1, 149.7, 140.4, 140.2, 121.2, 91.0, 75.9, 69.7, 58.0, 40.7, 36.0, 23.6;

III. Preparation of Various Nicotine Immunogens (Nicotine-linker-carrier Protein) (Scheme 9)

General Procedure for the Coupling of Carboxylic Acids to Keyhole Limpet Hemocyanin (KLH).

A solution of 1-(3-dimethylaminopropyl)-3-ethylcarbodiimide hydrochloride (EDC) (9 equiv) and distilled H₂O (500 μL) was added to a mixture of the acid (1 equiv) in distilled H₂O (500 μL) at 0° C. After 10 min a mixture of KLH (the same amount (mg) as of the acid) in distilled H₂O (1 mL) was added. The reaction mixture was kept at 0° C. for 10 min and then at ambient temperature over night. The pH of the reaction mixture was maintained at pH 4.5–6 during the reaction. The protein conjugate was purified by column chromatography [Sephadex G-25M, (PD-10 column), eluted with distilled H₂O] and then freeze-dried.

General Procedure for the Coupling of Amines to KLH.

A mixture of KLH (the same amount (mg) as of the amine) and H₂O (1 mL) was added to a mixture of the amine (10 mg) in H₂O (500 μL) at 0° C. A solution of EDC (9 equiv) in H₂O (500 μL) was added to the reaction mixture and the mixture was kept at 0° C. for 10 min and at ambient temperature over night. The pH of the reaction mixture was maintained at pH 4.5–6 during the reaction. The protein conjugate was purified by column chromatography [Sephadex G-25M, (PD-10 column), eluted with distilled H₂O] and then freeze-dried.

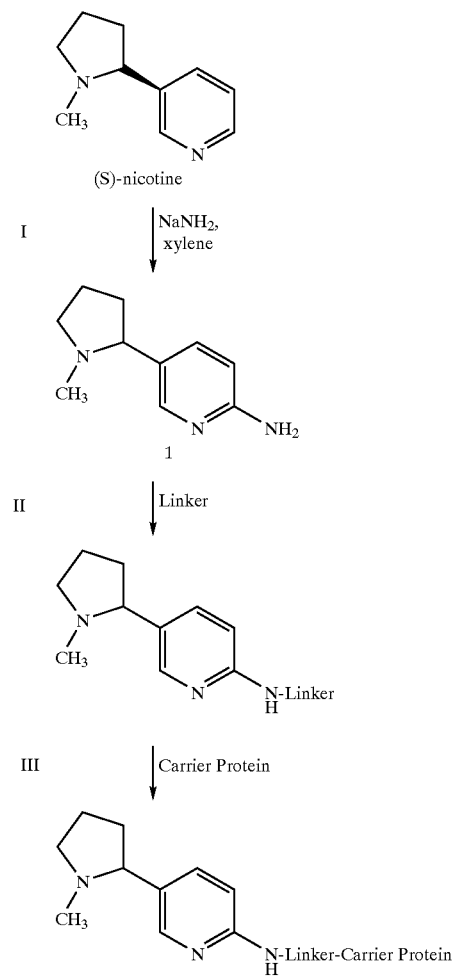

Scheme 1.
Preparation of nicotine immunogens

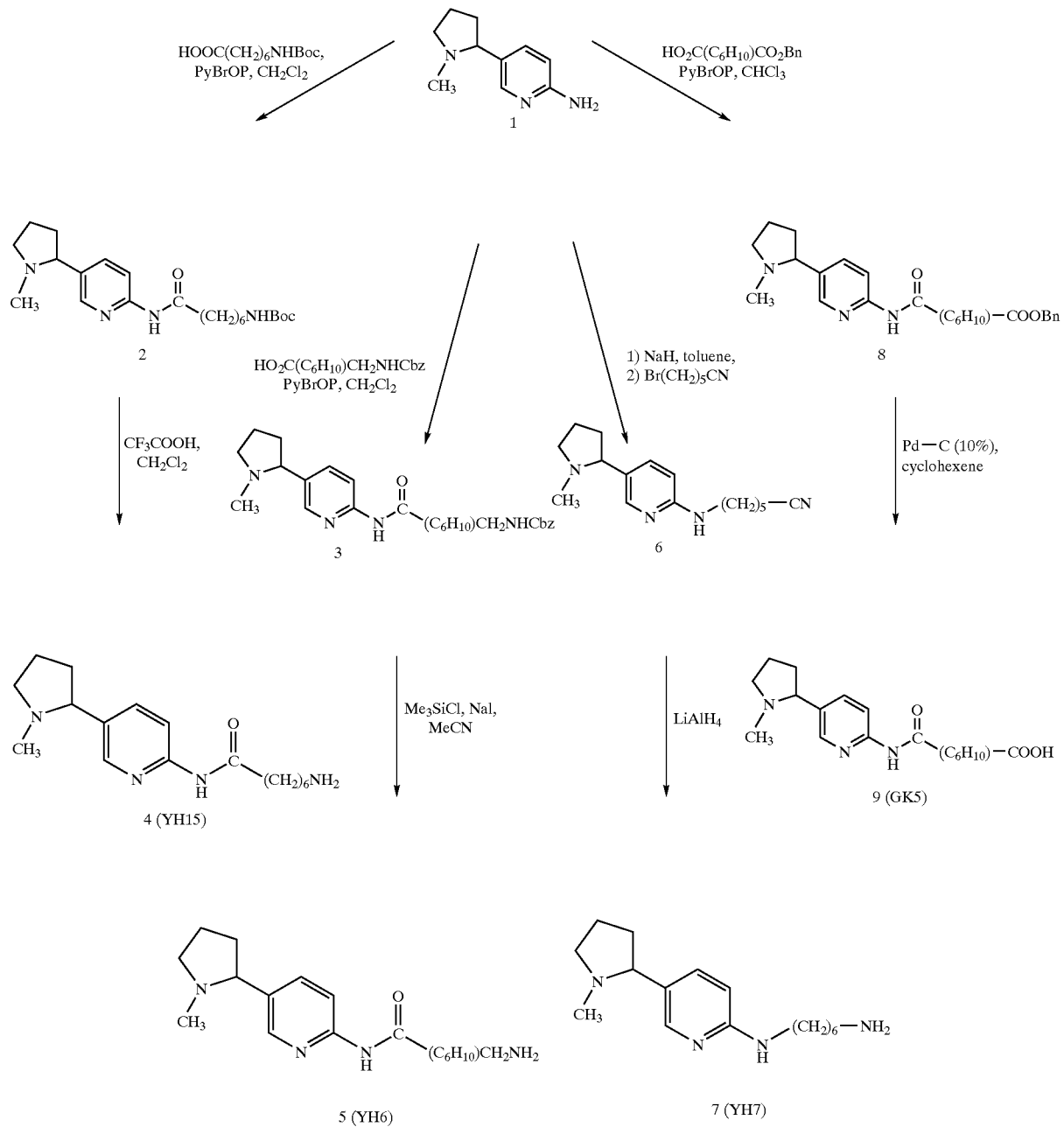

Scheme 3.
Synthesis of a 5-aminonicotine derivative.
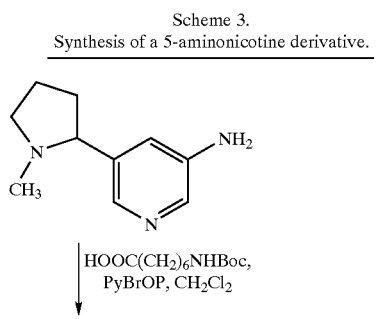
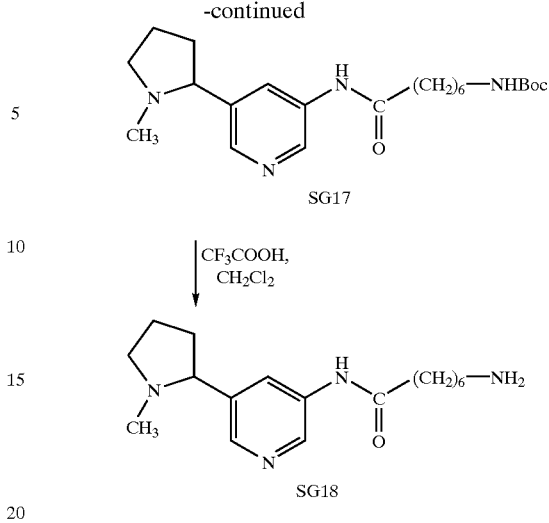
Scheme 4.
Synthesis of some linkers
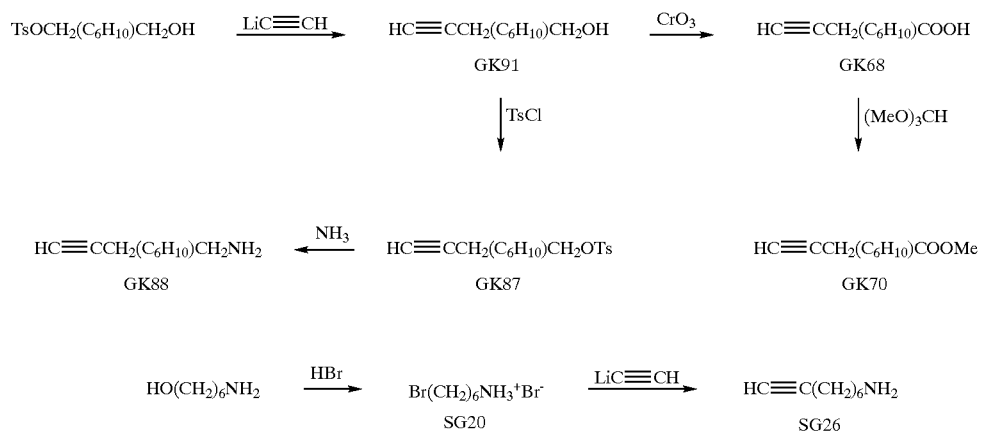

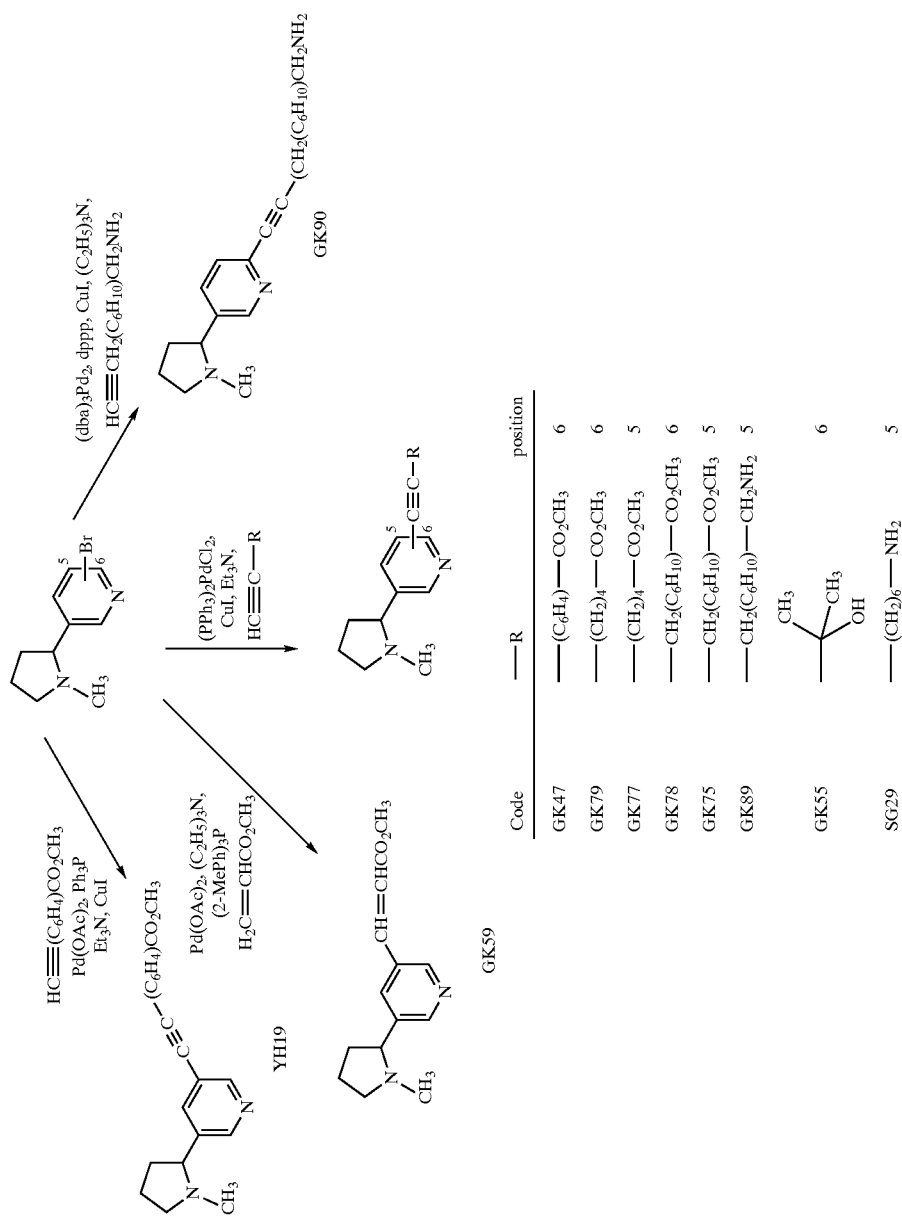

Scheme 6.
Hydrolysis of esters.

I.

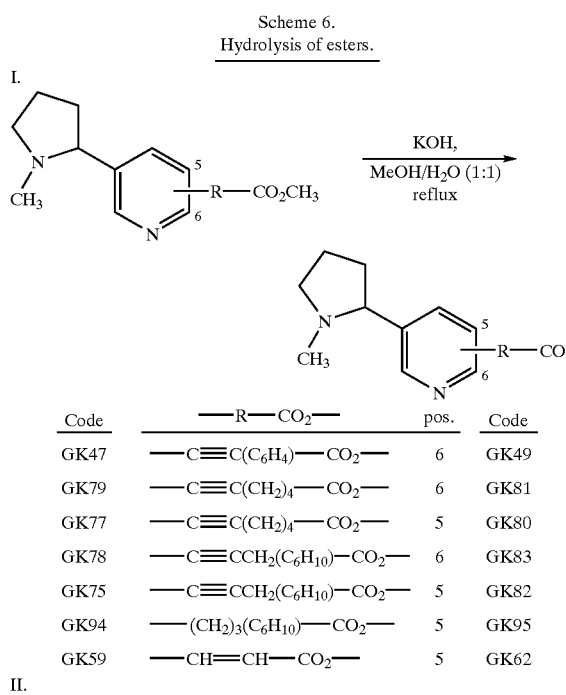

| Code | —R—CO$_2$— | pos. | Code |
|------|------------|------|------|
| GK47 | —C≡C(C$_6$H$_4$)—CO$_2$— | 6 | GK49 |
| GK79 | —C≡C(CH$_2$)$_4$—CO$_2$— | 6 | GK81 |
| GK77 | —C≡C(CH$_2$)$_4$—CO$_2$— | 5 | GK80 |
| GK78 | —C≡CCH$_2$(C$_6$H$_{10}$)—CO$_2$— | 6 | GK83 |
| GK75 | —C≡CCH$_2$(C$_6$H$_{10}$)—CO$_2$— | 5 | GK82 |
| GK94 | —(CH$_2$)$_3$(C$_6$H$_{10}$)—CO$_2$— | 5 | GK95 |
| GK59 | —CH=CH—CO$_2$— | 5 | GK62 |

II.

| Code | —R—CO$_2$— | pos. | Code |
|------|------------|------|------|
| YH19 | —C≡C(C$_6$H$_4$)—CO$_2$— | 5 | YH20 |
| YH22 | —(CH$_2$)$_2$(C$_6$H$_4$)—CO$_2$— | 5 | YH24 |

Scheme 7.
Hydrogenation of triple bond.

I.

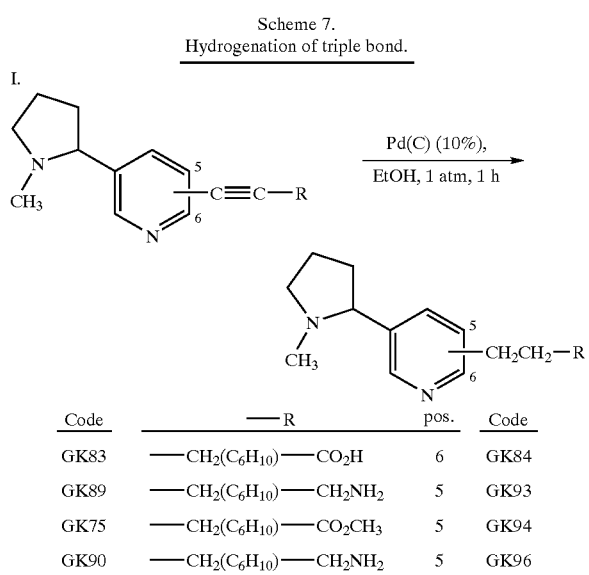

| Code | —R | pos. | Code |
|------|-----|------|------|
| GK83 | —CH$_2$(C$_6$H$_{10}$)—CO$_2$H | 6 | GK84 |
| GK89 | —CH$_2$(C$_6$H$_{10}$)—CH$_2$NH$_2$ | 5 | GK93 |
| GK75 | —CH$_2$(C$_6$H$_{10}$)—CO$_2$CH$_3$ | 5 | GK94 |
| GK90 | —CH$_2$(C$_6$H$_{10}$)—CH$_2$NH$_2$ | 5 | GK96 |

II.

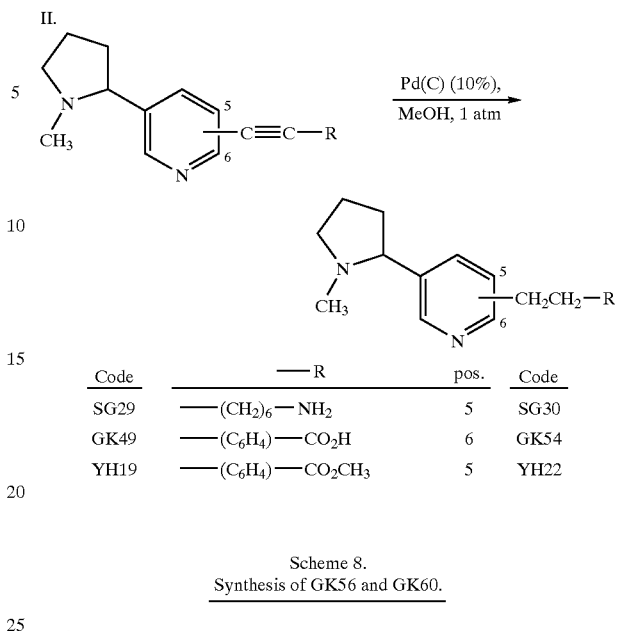

| Code | —R | pos. | Code |
|------|-----|------|------|
| SG29 | —(CH$_2$)$_6$—NH$_2$ | 5 | SG30 |
| GK49 | —(C$_6$H$_4$)—CO$_2$H | 6 | GK54 |
| YH19 | —(C$_6$H$_4$)—CO$_2$CH$_3$ | 5 | YH22 |

Scheme 8.
Synthesis of GK56 and GK60.

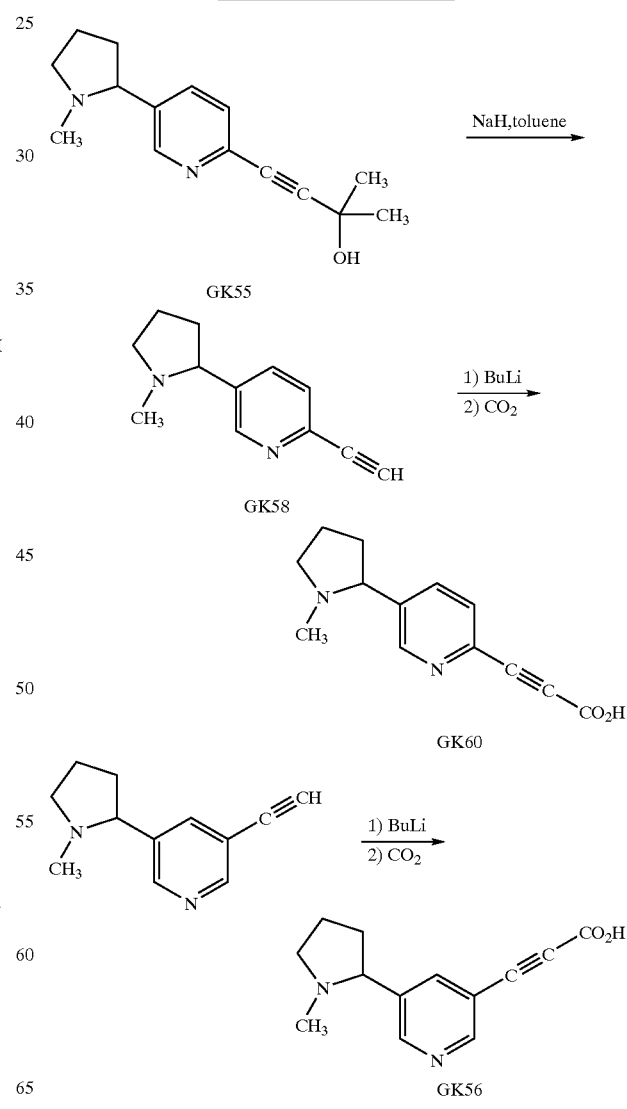

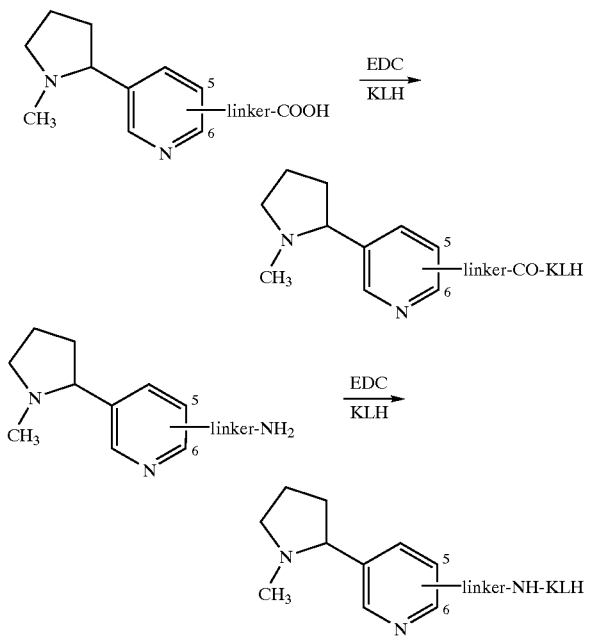

Scheme 9.
Synthesis of nicotine-linker-KLH derivatives (nicotine immunogens).

DESCRIPTION OF EXPERIMENTS

Materials and Methods

Animals

Male Wistar rats were housed in groups of 2–3 under standard laboratory conditions and maintained under a 12 hr light and dark cycle (lights on at 0600 hr) with unlimited access to food and water.

Immunization Procedures

Three immunization protocols were used:
1. Animals were immunized daily for five days, then rested for two days, and again immunized daily for five days. Each immunization injection contained 10 μg antigen (nicotine-linker-KLH conjugate) in 0.1 ml saline and was administered subcutaneously (s.c.) in the posterior neck region of the body. Controls were injected with either 10 μg KLH in 0.1 ml saline or 0.1 ml saline alone.
2. Animals were immunized using 100 μg antigen (nicotine-linker-KLH conjugate) and Freund's complete adjuvant in a bolus injection and then given a booster injection on day 11 or 14, containing 100 μg antigen (nicotine-linker-KLH conjugate) and Freund's incomplete adjuvant; these injections were given i.p in 0.4 ml. Controls were injected with either 100 μg KLH in Freund's complete adjuvant or Freund's complete adjuvant alone. In the booster injections Freund's incomplete adjuvant was used in stead of Freund's complete adjuvant.
3. Nicotine self-administering animals were immunized using 100 μg antigen (nicotine-linker-KLH conjugate) and Freund's complete adjuvant in a bolus injection and then given a booster injection on day 7 or 8, containing 100 μg antigen (nicotine-linker-KLH conjugate) and Freund's incomplete adjuvant; these injections were given i.p in 0.4 ml.

Elisa

Elisa-plates (Sigma or Labsystems) were coated with a nicotine-linker-BSA conjugate. When required the plates were blocked using a solution of 3% BSA in PBS. After extensive wash, serum was added in various dilutions (1:1 to 1:390625) and the plates incubated at 37° C. The plates were washed again and after adding the secondary antibody, an alkaline phosphatase conjugated goat anti-rat IgG (Sigma), they were further incubated at 37° C. The enzyme substrate p-nitrophenyl phosphate (p-NPP) (Sigma) produces a coloured end product that can be read spectrophotometrically at 405 nm.

Competitive Elisa

The competitive Elisa was performed as the ordinary Elisa with the exception that only a single dilution (1:3125) of serum was used. Nicotine, cotinine, nornicotine, nicotine-N-oxide and niacin respectively were used as competitors.

Electrophysiological Single-cell Recording of Dopamine Neurons in the VTA

Rats were anaesthetised using chloral hydrate (400 mg/kg, i.p.) with additional doses given when needed to maintain surgical anaesthesia throughout the experiment. Body temperature was maintained at 37° C. using a thermostatically controlled heating pad. A tracheal cannula and a jugular vein catheter were inserted before the animal was mounted in a David Kopf stereotaxic instrument. A hole was drilled above the recording area, i.e., AP +3.0, measured from lambda, and ML±0.7 mm (Paxinos and Watson, 1986). Electrodes were pulled from Omegadot glass capillaries and filled with Pontamine Sky Blue (2%) in 2 M sodium acetate. The tips were broken under microscope, yielding an impedance of approximately 2.0 MΩ measured at 135 Hz. Presumed DA neurones were found 7.5–8.5 mm from brain surface with characteristics of previously histochemically identified DA neurones (Grace and Bunney, 1983; Wang, 1981), i.e., typical triphasic spike waveforms of more than 2.0 ms duration and basal firing rates of 1–10 Hz. Extracellular action potentials were amplified, discriminated and monitored on an oscilloscope and an audiomonitor. Discriminated spikes were fed, via a Cambridge Electronics design 1401 interface, into an AST Bravo LC 4/66d computer with Spike 2 software. Analysis of the temporal pattern of firing of the DA neurones was performed off-line with a custom analysis script developed in our laboratory. Burst firing, firing rate, and variation coefficient were calculated over a period of 250 consecutive inter-spike time intervals. The onset of a burst was defined as an interval shorter than 80 ms and burst termination at the next interval exceeding 160 ms (Grace and Bunney, 1984). Burst firing was quantified as the percentage ratio between spikes in bursts and the total number of spikes. Variation coefficient was defined as the percentage ratio between the standard deviation and the mean value of the inter-spike intervals (Werner and Mountcastle, 1963).

Nicotine was administered i.v. in the dose range 3–100 μg/kg, cumulative dose, with doubling of the dose for each step. Nicotine injections were given every 3–5 min. At the end of each experiment a negative current of 5 μA was passed for 10 min through the electrode to mark the recording site (Lodge et al., 1974). The animals were killed by an overdose of chloral hydrate and the brains were preserved in 5% formaldehyde in 25% sucrose and later sliced on a microtome in 50 μm thick sections and stained with neutral red for histological verification of recording sites. Only recording sites located within the VTA were accepted in this protocol.

Voltammetry

Voltammetric measurements of dopamine were performed in rats pre-treated with pargyline and kept under chloral hydrate anaesthesia. The active part of the carbon fibre electrode was 12 ∞m thick and 500 μm long. Electrodes were prepared and treated as described by Gonon (1988). Electrodes were positioned at the coordinates: AP=+1.6 and ML=±0.8 for the $NAC_{shell}$ (Paxinos and Watson, 1986). The tip of the electrode was placed 6.5–7.0 mm below cortical surface and differential normal pulse voltarmmetry was used to record voltammograms every min with parameters described previously (Gonon et al., 1984 and Gonon, 1988). When a stable baseline was observed the animal was injected iv. with saline and thereafter nicotine in increasing doses (6, 12, 24 and 48 μg/kg) administered at 10 min intervals.

EXAMPLES

At present, 16 different nicotine immunogens have been tested for immunogenicity using both in vitro and in vivo methods.

Example 1
Elisa

Rats immunized with GK5-KLH conjugate according to protocol 2 were used. Blood samples for Elisa experiments were collected 7 or 9 days after the first bolus immunization. The Elisa antibody titers ranged between 1:100 and 1:15000, see FIG. 1.

Figure 2:
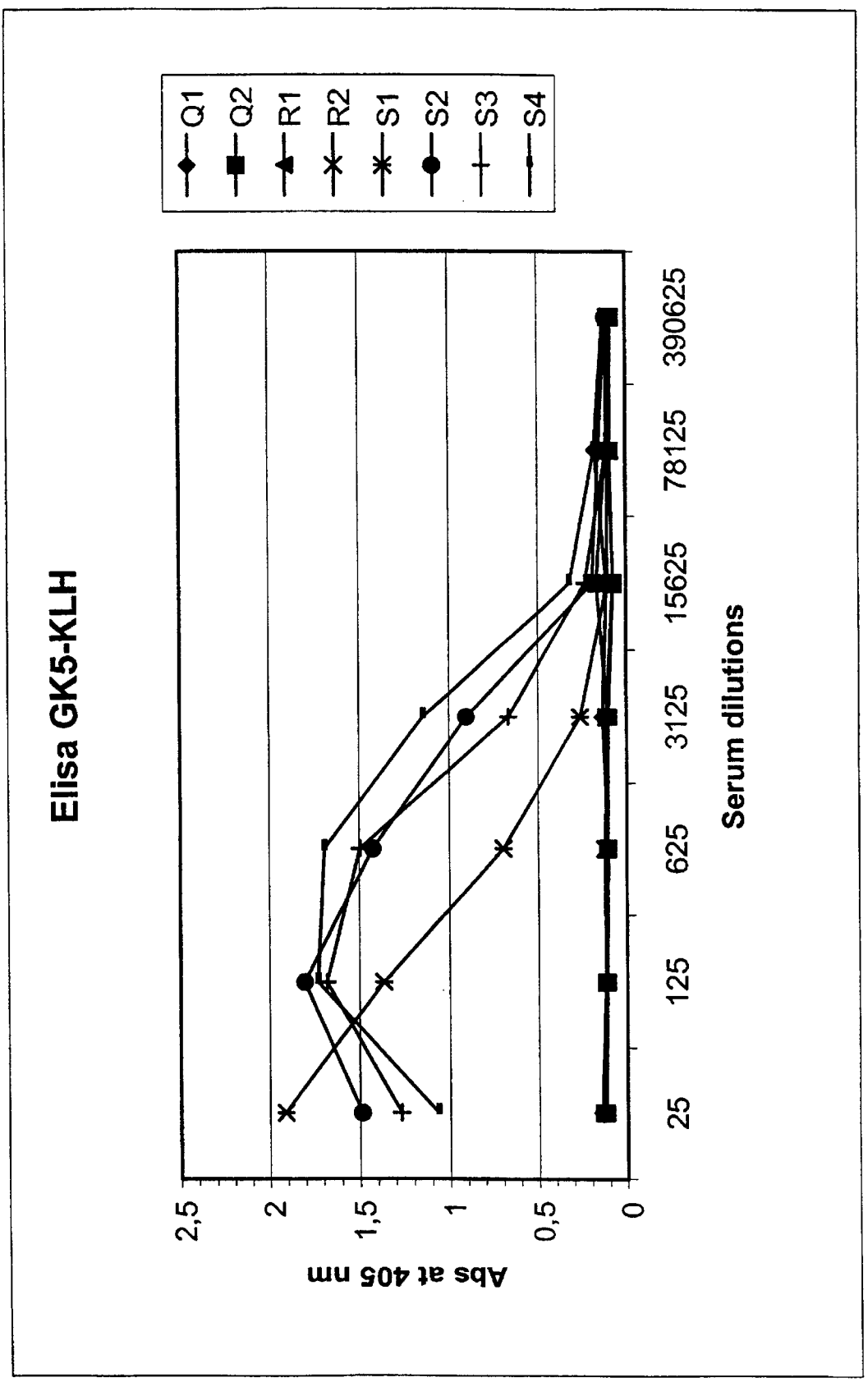
FIG. 2. Elisa measurements on serum from immunized rats collected 1–4 days after booster immunization with GK5-KLH.

Blood samples were again collected on day 1–4 post-booster immunization. This second immunisation gave titers between 1:3000 to 1:15 500, see FIG. 2.

Example 2
Elisa

Figure 3:
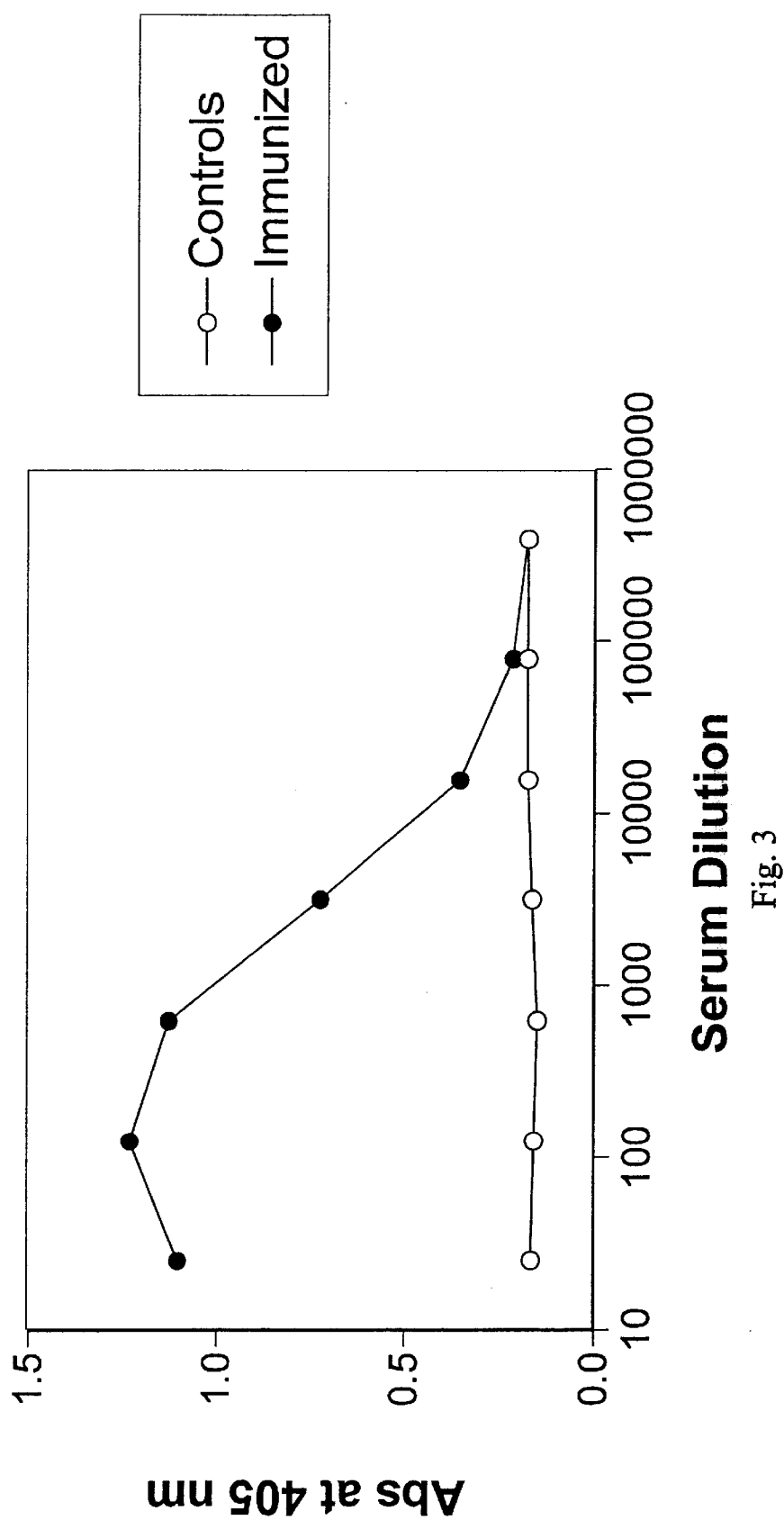
FIG. 3. Elisa titre measurements of serum from immunized rats. The titre of specific antibodies from GK60-KLH immunized rats is 1:4000. Immunization using other immunogens gave similar results.

After immunization with GK5-KLH using immunization protocol 1, serum from experimental animals were collected and the specific antibody titres were typically 1:500–1:3000 measured with Elisa technique. Immunization protocol 2, which included an adjuvant, resulted in a higher titre of specific antibodies, typically 1:3000–1:15 000, see FIG. 3. All tested nicotine immunogens, e.g. GK5-KLH, GK60-KLH, YH6-KLH, GK84-KLH and GK80-KLH, were immunized using protocol 2. The titres were stable for at least one month.

Example 3
Competitive Elisa

Figure 4:
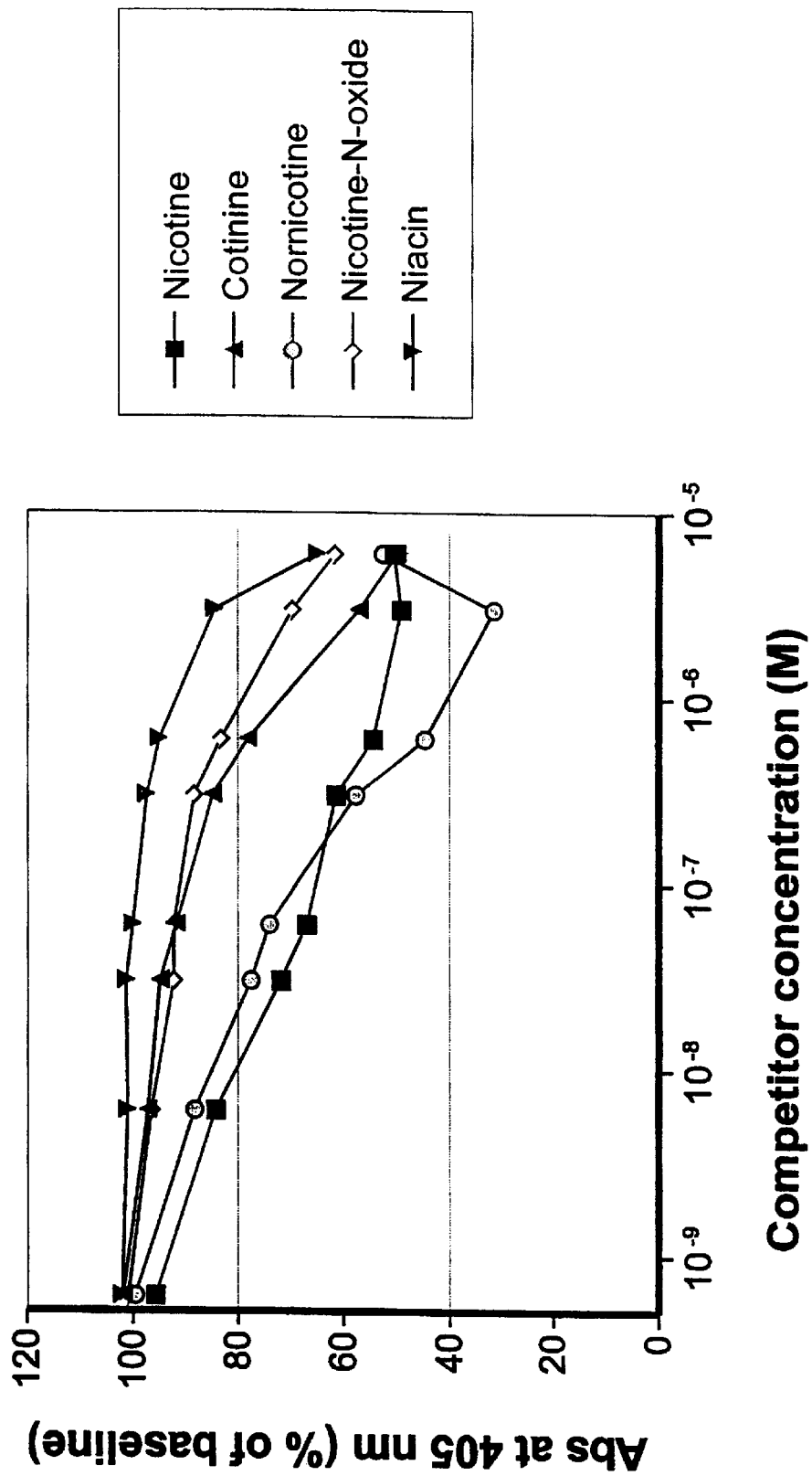
FIG. 4. Competitive Elisa. Immunogen GK-84-KLH immunized using protocol 2 gave rise to antibodies that were about 100 times more specific to nicotine and nornicotine than to the other competitors used.

Competitive Elisa was performed on the serum samples from immunized rats. Nicotine, the metabolites cotinine, nornicotine, nicotine-N-oxide and niacin (not metabolite) were used as competitors. The competitor concentration ranged from $6 \times 10^{-10}$ to $6 \times 10^{-6}$ M. After immunization using protocol 2 immunogens gave rise to antibodies that were more specific to nicotine than to cotinine, nicotine-N-oxide and niacin, see FIG. 4. In most cases the specificity for nicotine and nornicotine were similar. Cotinine is the major nicotinic metabolite (80%) (Benowitz et al. 1994) therefor it is important that the nicotinic antibodies have a greater specificity towards nicotine than cotinine, on the other hand only 0.4% of the nicotine is metabolised into nornicotine (Benowitz et al. 1994) whereas the similarity in specificity towards nicotine and nornicotine should not play a significant role.

Example 4
Electrophysiology

Electrophysiological single-cell recordings from rat ventral tegmental area dopamine neurones revealed that when nicotine was administered intravenously (3–48 μg/kg), dopamine cells in control (KLH immunized) rats generally responded with an increase in average firing rate and burst firing (see FIG. 5), as well as a deregularization of the firing pattern, as assessed by the variation coefficient. Five out of six rats tested responded to nicotine. The changes were already evident in doses of nicotine as low as 6 μg/kg. In three out of six rats, the activation was accompanied by a transient (i.e. <1 min) but pronounced increase in neuronal activity immediately following drug administration. Out of these, two cells which did not display bursts before nicotine were converted to a bursty pattern after nicotine administration (6 μg/kg).

Figure 6:
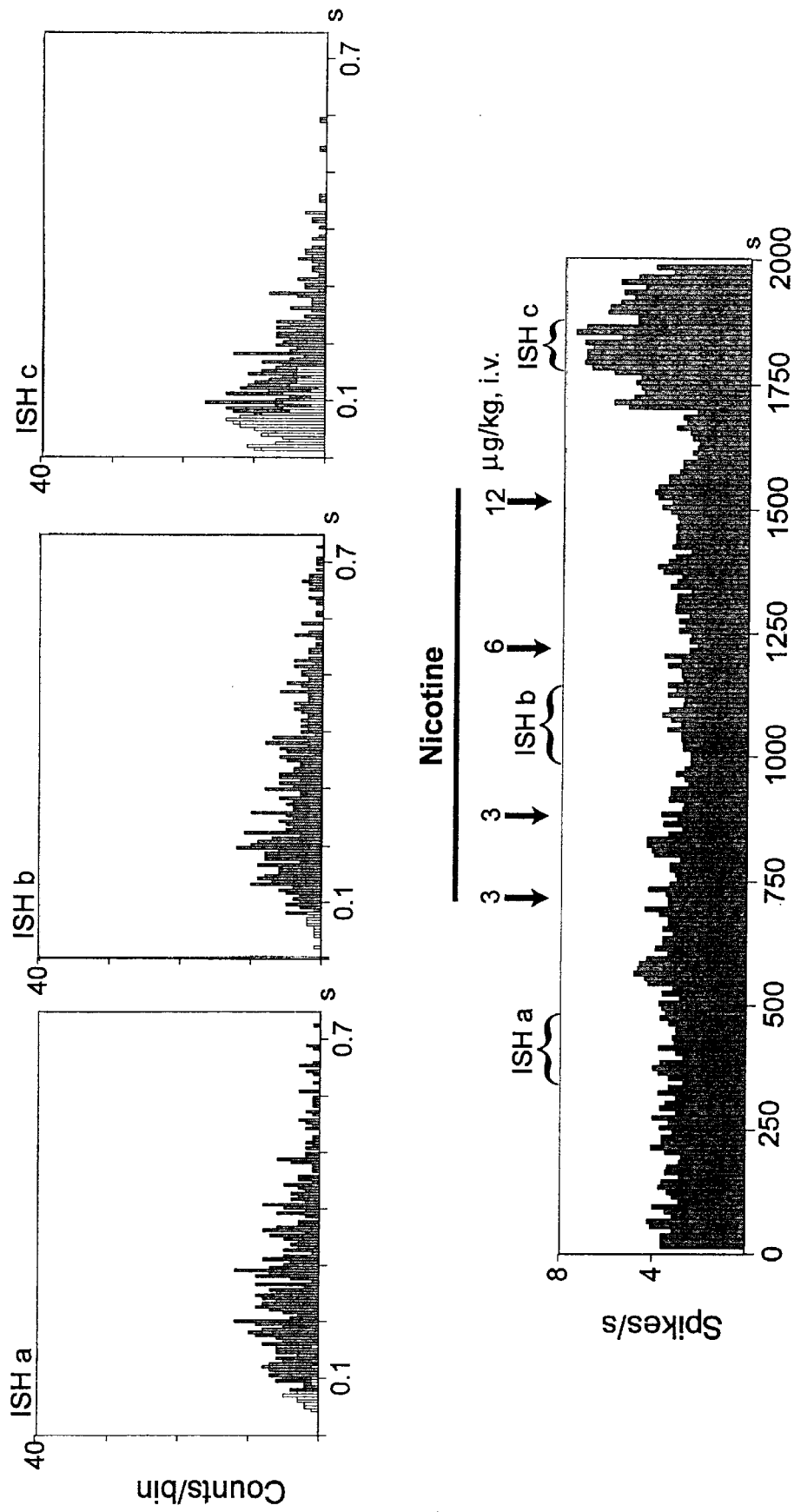
FIG. 6. Electrophysiological single-cell recordings from VTA DA neurones in immunized rats. The DA cells appear less sensitive to the activating effects of nicotine after immunization.

In contrast, only one out of four rats immunized with GK5-KLH using immunization protocol 1 responded to nicotine with an increase in dopamine neuronal activity. In addition, transient increases in neuronal activity were not observed, neither was conversion of a non-bursty firing pattern to a bursty one, even when very high doses of nicotine were administered (see FIG. 6).

Generally, immunized rats thus appear less sensitive to the activating effects of nicotine on ventral tegmental area dopamine neuronal activity. Specifically, immunized rats were not activated by low doses (i.e. <12 μg/kg) of nicotine like non-immunized rats, and cells did not either respond with an immediate activation in response to systemic injections of nicotine, as was generally seen in control animals.

In conclusion, these experiments demonstrate that the immunogen used is effective in largely preventing the acute stimulation of burst firing in the mesolimbic dopamine neurons after administration of small nicotine doses equivalent to those ingested by smoking one or two cigarettes. Since the acute effect of e.g. a puff on the brain's reward systems in all probability represents the reinforcing unit in tobacco smoking, this compound looks indeed promising.

Example 5
Voltammetry

Figure 7B:
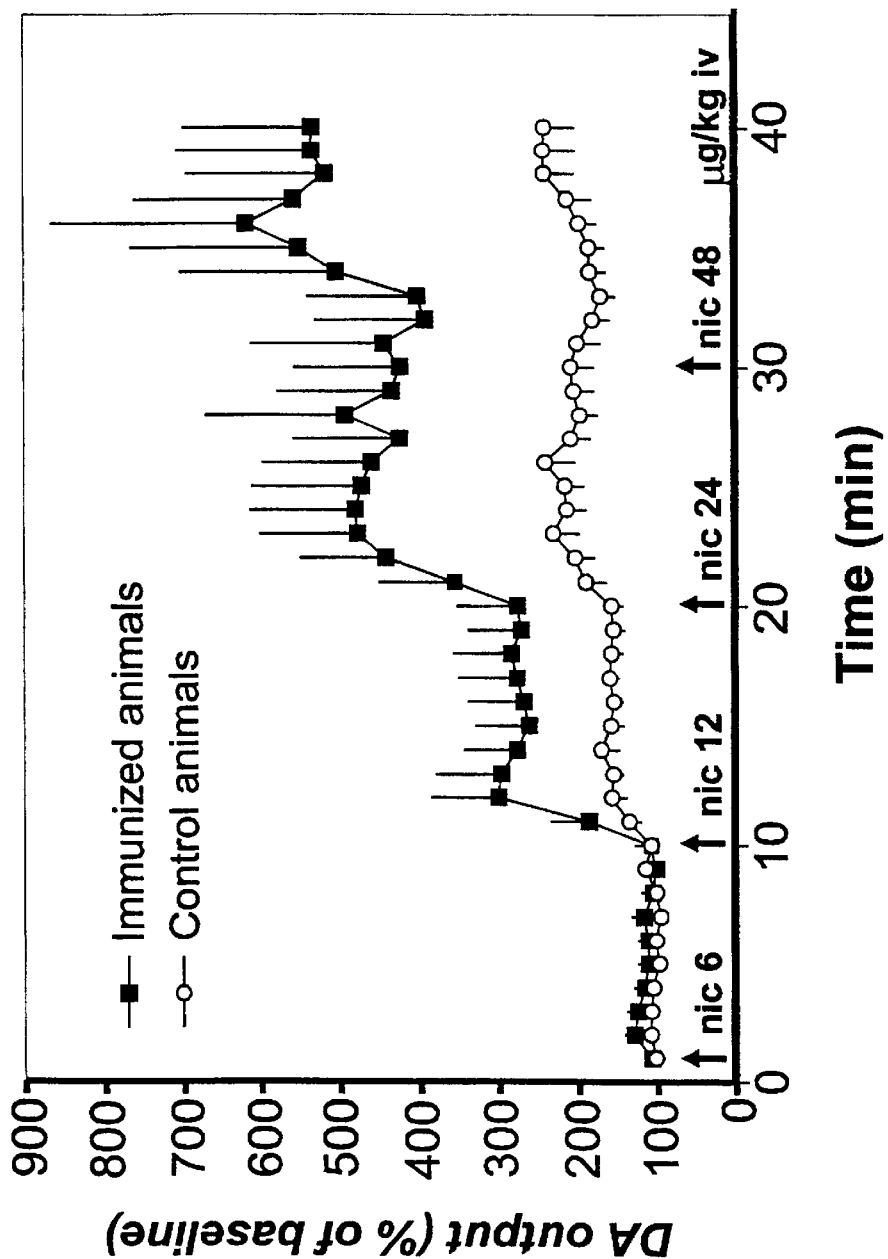
FIG. 7b. Active immunization using immunogen GK80-KLH results in a marked increase on the dopamine overflow in nucleus accumbens shell after nicotine administration compared to controls.
Figure 7C:
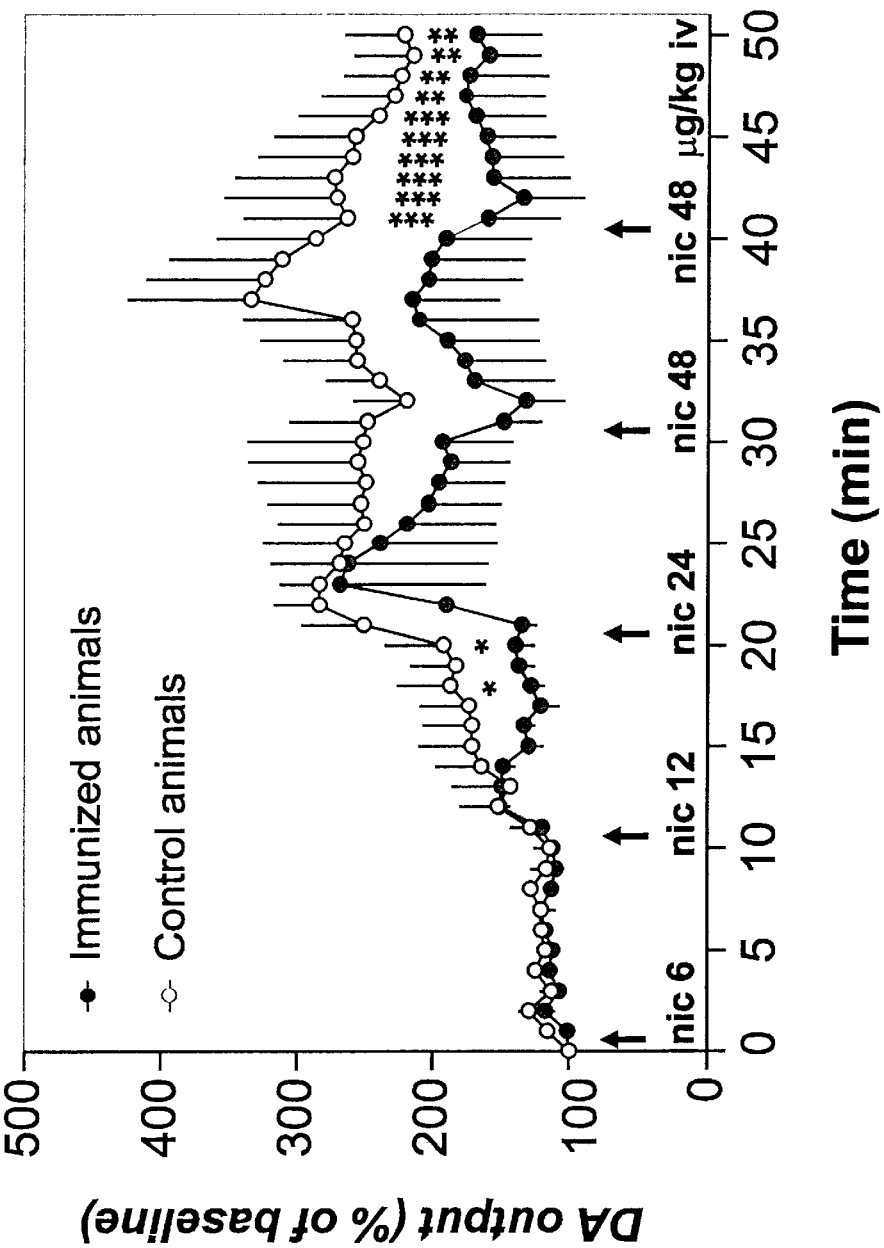
FIG. 7c. The effect of the immunization with immunogen YH6-KLH on nicotine-induced dopamine output is stable over a three week period. *p=0.05; p=0.01; *p=0.001.

In the controls nicotine administration gives rise to a dose dependent increase of DA-output in the nucleus accumbens shell. In contrast active immunization alters the nicotinic effect on the DA-overflow, see FIGS. 7a, b and c. Depending on the properties of the immunogen, i.e. the nicotinic hapten, the effect of nicotine on the dopamine output can be suppressed to baseline levels (FIG. 7a) or instead even paradoxically increased (FIG. 7b). In studies (FIG. 7c) where the immunization occurred already 3 weeks before the actual experiment with nicotine, animals still displayed a marked reduction in the central effect of nicotine even in high doses on the mesolimbic dopamine system, i.e. the primary reward pathway in the brain, which has proven critical for self administration of nicotine and its dependence liability.

REFERENCES IN THE DESCRIPTION OF EXPERIMENTS

Benowitz N. L., Jacob P., Fong I., and Gupta S.: Nicotine maetabolic profile in man: Comparison of cigarette smoking and transdermal nicotine. J. Pharmacol. Exp. Ther. 268: 296–303, 1994.

Gonon F., Buda M. and Pujol J. F.: Treated carbonfiber electrodes for measuring cathchols and ascorbic acid. In Marsden Calif. (ed) Measurement of neurotransmittor release in vivo. Wiley, Chichester, pp 153–171, 1984.

Gonon F. G.: Non-linear relationship between impulse flow and dopamine release by rat midbrain dopaminergic neurones as studied by in vivo electrochemistry. Neuroscience 24:19–28, 1988.

Grace A. A. and Bunney B. S.: Intracellular and extracellular electrophysiology of nigral dopaminergic neurones.

I. Identification and characterization. Neuroscience 10:301–315, 1983.

Grace A. A. and Bunney B. S.: The control of firing pattern in nigral dopamine neurones: burst firing. J Neurosci 4:2877–2890, 1984.

Lodge D., Caddy K. W. T., Headley P. M., and Biscoe T. J.: The locations of neurones with pontamine sky blue. Neuropharmacology 13:481–485, 1974.

Paxinos G. and Watson C.: The rat brain in stereotaxic coordinates, $2^{nd}$ ed. Academic Press, London, 1986.

Wang R. Y.: Dopaminergic neurones in the rat ventral tegmental area. I. Identification and characterization. Brain Res Rev 3:123–140, 1981.

Werner G. and Mountcastle V. B.: The variability of central neuronal activity in a sensory system, and its implications for the central reflection of sensory events. J Neurophysiol 26:958–977, 1963.

What is claimed is:

1. A nicotine immunogen comprising a 5- or 6-nicotinyl-linker-carrier protein having the formula

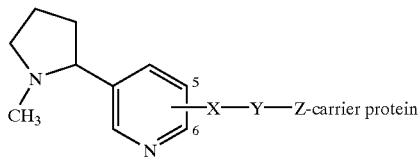

wherein

X is —C≡C— or —CH=CH—,

Y is —$(CH_2)_k$— or —$(CH_2)_m$—$C_6H_{10}$—$(CH_2)_n$— or —$(CH_2)_m$—$C_6H_4$—$(CH2)_n$— wherein k=0–20, m=0–6, and n=0–6, when

Z is —NH— or CO— or

X is —$CH_2$—,

Y is —$(CH_2)_m$—$C_6H_{10}$—$(CH_2)_n$— or —$(CH_2)_m$—$C_6H_4$—$(CH_2)_n$— wherein m=0–6, and n=0–6, and

Z is —NH— or —CO—.

2. The nicotine immunogen according to claim 1, wherein the carrier protein is selected from the group consisting of keyhole limpet hemocyanin (KLH), tetanus toxoid, diphtheria toxoid, non-toxic mutant diphtheria toxoid $CRM_{197}$, outer membrane protein complex (OMPC) from Neisseria meningitidis, the B subunit of heat-labile *Escherichia coli*, and recombinant exoprotein A from *Pseudomonas aeruginosa* (rEPA).

3. A 5- or 6-nicotinyl-linker-carrier protein having the formula

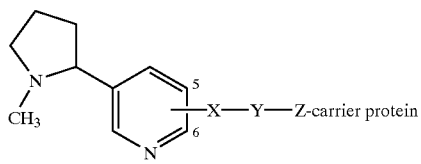

wherein

X is —C≡C— or —CH=CH—,

Y is —$(CH_2)_k$— or —$(CH_2)_m$—$C_6H_{10}$—$(CH_2)_n$— or —$(CH_2)_m$—$C_6H_4$—$(CH_2)_n$— wherein k=0–20, m=0–6, and n=0–6, and

Z is —NH— or —CO— or

X is —$CH_2$—,

Y is —$(CH_2)_m$—$C_6H_{10}$—$(CH_2)_n$— or —$(CH_2)_m$—$C_6H_4$—$(CH_2)_n$— wherein m=0–6, and n=0–6, when

Z is —NH or —CO—.

4. A 5- or 6-nicotinyl-linker-carrier protein according to claim 3, wherein the carrier protein is selected from the group consisting of keyhole limpet hemocyanin (KLH), tetanus toxoid, diphtheria toxoid, non-toxic mutant diphtheria toxoid $CRM_{197}$, outer membrane protein complex (OMPC) from Neisseria meningitidis, the B subunit of heat-labile *Escherichia coli*, and recombinant exoprotein A from *Pseudomonas aeruginosa* (rEPA).

5. A 5- or 6-nicotinyl-linker-carrier protein according to claim 3 for use as a medicament.

6. Pharmaceutical composition comprising a 5- or 6-nicotinyl-linker-carrier protein according to claim 4 and a pharmaceutically acceptable vehicle.

7. Pharmaceutical composition according to claim 6 further comprising an adjuvant.

8. A 5- or 6-nicotinyl-linker-carrier protein according to claim 4 for use as a medicament.

9. Pharmaceutical composition comprising a 5- or 6-nicotinyl-linker-carrier protein according to claim 5 and a pharmaceutically acceptable vehicle.

* * * * *